United States Patent [19]

Schmaljohn et al.

[11] Patent Number: 5,614,193
[45] Date of Patent: Mar. 25, 1997

[54] HANTAVIRUS VACCINE

[75] Inventors: Connie S. Schmaljohn; David J. McClain, both of Frederick; Joel Dalrymple, deceased, late of Myersville, all of Md., by Lonnie Dalrymple, Legal Representative

[73] Assignee: The United States of America as represented by the Secretary of the Army, Washington, D.C.

[21] Appl. No.: 218,943

[22] Filed: Mar. 28, 1994

Related U.S. Application Data

[63] Continuation-in-part of Ser. No. 799,479, Nov. 14, 1991, Pat. No. 5,298,423.

[51] Int. Cl.$^6$ ............... A61K 39/285; A61K 39/12; C12N 7/01
[52] U.S. Cl. ................. 424/186.1; 424/199.1; 424/204.1; 424/232.1; 435/235.1; 435/320.1; 935/65
[58] Field of Search ............... 424/186.1, 199.1, 424/204.1, 232.1; 935/65; 435/235.1, 320.1

[56] References Cited

PUBLICATIONS

Lee et al. "Isolation of the Etiologic Agent of Korean Hemorrhagic Fever", *J. Infect. Dis.* 137:298–307 (1978).
Schmaljohn and Dalrymple "Analysis of Hantaan Virus RNA: Evidence for a New Genus of Bunyavirdae", *Virology* 131:482–491 (1983).
Schmaljohn et al. "Coding Strategy of the S Genome Segment of Hantaan Virus", *Virology* 155:633–643 (1986).
Schmaljohn et al. "Hantaan Virus M RNA: Coding Strategy, Nucleotide Sequence, and Gene Order", *Virology* 157:31–39 (1987).
Yoo and Kang "Nucleotide sequence of the M segment of the genomic RNA of Hantaan virus 76–118", *Nuc. Acids Res.* 15:6299–6300 (1987).
Schmaljohn et al. "Baculovirus Expression of the Small Genome Segment of Hantaan Virus and Potential Use of the Expressed Nucleocapsid Protein . . . ", *J. Gen. Virol.* 69:777–786 (1988).
Rossi et al. "Diagnostic potential of a baculovirus–expressed nucleocapsid protein for hantaviruses", *Arch. Virol.* S1:19–28 (1990).
Schmaljohn et al. "Antigenic Subunits of Hantaan Virus Expressed by Baculovirus and Vaccinia Virus Recombinants", *J. Virol.* 64:3162–3170 (1990).
Schmaljohn et al. "Preparation of candidate vaccinia–vectored vaccines for haemorrhagic fever with renal syndrome", *Vaccine* 10:10–13 (1992).
Hsiang, C.M. 1989, Virus Genes vol. 2 pp. 367–369.
Tartaglia, J. et al, 1990. Crit Rev. Immunol. vol. 10 pp. 13–30.
Xu, X. et al. Am. J. Trop. Med. Hyg. vol. 47 pp. 397–404.

*Primary Examiner*—Mary E. Mosher
*Attorney, Agent, or Firm*—John Francis Moran

[57] ABSTRACT

Vaccine formulations for inducing protective immune response to Hantaviruses in humans are disclosed. These formulations include an attenuated vaccinia virus vector containing cDNA's encoding Hantavirus nucleocapsid N protein, G1 and G2 glycoproteins. Methods for the use of these formulations also are disclosed.

28 Claims, 8 Drawing Sheets

FIG. 1-1

[MET GLY GLY ILE TRP LYS TRP LEU VAL MET ALA SER LEU VAL TRP PRO VAL LEU] THR LEU ARG ASN VAL TYR ASP MET LYS ILE
GLU CYS PRO HIS THR VAL SER PHE GLY GLU ASN SER VAL ILE GLY TYR VAL GLU LEU PRO PRO VAL PRO LEU ALA ASP THR ALA
5 GLN MET VAL PRO GLU SER SER CYS ASN MET ASP ASN HIS GLN SER LEU ASN THR ILE THR LYS TYR THR GLN VAL SER TRP ARG
GLY LYS ALA ASP GLN SER SER GLN SER ASN SER PHE GLU THR VAL SER THR GLU VAL ASP LEU LYS GLY THR CYS VAL
LEU LYS HIS LYS MET VAL GLU GLU SER TYR ARG SER ARG LYS SER VAL THR CYS TYR ASP LEU SER CYS ASN SER THR TYR CYS
LYS PRO THR LEU TYR MET ILE VAL PRO ILE HIS ALA CYS ASN MET MET LYS SER CYS LEU ILE ALA LEU GLY PRO TYR ARG VAL
GLN VAL VAL TYR GLU ARG SER TYR CYS MET THR GLY VAL LEU ILE GLU GLY LYS CYS PHE VAL PRO ASP GLN SER VAL VAL
10 SER ILE ILE LYS HIS GLY ILE PHE ASP ILE ALA SER VAL HIS ILE VAL CYS PHE PHE VAL ALA VAL LYS GLY ASN THR TYR LYS ILE
PHE GLU GLN VAL LYS LYS SER PHE GLU SER THR CYS ASN ASP THR GLU ASN LYS VAL GLN GLY TYR TYR ILE CYS ILE VAL GLY
ASN SER ALA PRO ILE TYR VAL PRO THR LEU ASP ASP PHE ARG SER MET GLU ALA PHE THR GLY ILE PHE ARG SER PRO HIS GLY
GLU ASP HIS ASP LEU ALA GLY GLU GLU ILE ALA GLY GLU ILE ALA SER TYR SER ILE VAL GLY PRO ALA ASN ALA LYS VAL PRO HIS SER ALA SER
SER ASP THR LEU SER LEU ILE ALA TYR SER GLY ILE PRO SER TYR SER SER SER LEU THR SER SER THR GLU ALA LYS LYS

FIG. 1-2

15 HIS VAL PHE SER PRO GLY LEU PHE PRO LYS LEU ASN HIS THR ASN CYS ASP LYS SER ALA ILE PRO LEU ILE TRP THR GLY MET
   ILE ASP LEU PRO GLY TYR TYR GLU ALA VAL HIS PRO CYS THR VAL PHE CYS VAL LEU SER GLY PRO GLY ALA SER CYS GLU ALA
   PHE SER GLU GLY GLY ILE PHE ASN ILE THR SER PRO MET CYS LEU VAL SER LYS GLN ASN ARG PHE ARG LEU THR GLU GLN
   GLN VAL ASN PHE VAL CYS GLN ARG VAL ASP MET ASP ILE VAL VAL TYR CYS ASN GLY GLN ARG LYS VAL ILE LEU THR LYS
   THR LEU VAL ILE GLY GLN CYS ILE TYR THR ILE THR SER LEU PHE SER LEU PRO GLY VAL ALA HIS SER ILE ALA VAL GLU
20 LEU CYS VAL PRO GLY PHE HIS GLY PHE ILE LEU VAL THR PHE CYS PHE GLY TRP VAL LEU ILE PRO ALA
   ILE THR PHE ILE LEU THR VAL LEU LYS PHE ILE ALA ASN ILE PHE HIS THR SER ASN GLN GLU ASN ARG LEU LYS SER VAL
   LEU ARG LYS ILE LYS GLU GLU PHE GLY LYS THR LYS GLY LYS SER MET VAL CYS LYS TYR GLU CYS GLU THR TYR
   LYS GLU LEU LYS ALA HIS GLY VAL SER CYS PRO GLN SER GLN CYS PRO TYR CYS PHE THR HIS CYS GLU PRO THR GLU ALA ALA
   PHE GLN ALA HIS TYR LYS VAL CYS GLN VAL THR HIS ARG PHE ARG ASP ASP LEU LYS THR VAL THR PRO GLN ASN PHE THR
25 PRO GLY CYS TYR ARG THR LEU ASN LEU PHE ARG TYR LYS SER ARG CYS TYR ILE PHE THR MET TRP ILE PHE PHE LEU VAL LEU
   GLU SER ILE LEU TRP ALA ALA SER ALA

FIG. 2

SER GLU THR PRO LEU THR PRO VAL TRP ASN ASP ASN ALA HIS GLY VAL GLY SER VAL PRO MET HIS THR ASP LEU GLU LEU ASP
PHE SER LEU THR SER SER SER LYS TYR THR ARG ARG LYS LEU THR ASN PRO LEU GLU ALA GLN SER ILE ASP LEU HIS
5  ILE GLU ILE GLU GLN ILE GLY THR ILE GLY VAL ASP VAL HIS ALA LEU GLY HIS TRP PHE ASP GLY ARG LEU ASN LEU LYS THR SER
PHE HIS CYS TYR GLY ALA CYS THR LYS TYR GLU TYR PRO TRP HIS THR ALA LYS CYS HIS TYR GLU ARG ASP TYR GLN TYR GLU
THR SER TRP GLY CYS ASN PRO SER ASP CYS PRO GLY VAL GLY THR GLY CYS VAL GLY LEU TYR LEU ASP GLN LEU
LYS PRO VAL GLY SER ALA TYR LYS ILE ILE THR ILE ARG TYR SER ARG ARG VAL CYS VAL GLN PHE GLY GLU ASN LEU CYS
LYS ILE ILE ASP MET ASN ASP CYS PHE VAL SER ARG HIS VAL LYS VAL CYS ILE ILE GLY THR VAL SER LYS PHE SER GLN GLY
10 ASP THR LEU LEU PHE PHE GLY PRO LEU GLY GLY LEU ILE PHE LYS HIS TRP CYS THR SER THR CYS GLN PHE GLY ASP
PRO GLY ASP ILE MET SER PRO ARG ASP LYS PHE LEU CYS PRO GLU PHE PRO GLY SER PHE ARG LYS LYS CYS ASN PHE ALA
THR THR PRO ILE CYS GLU TYR ASP GLY ASN MET VAL SER GLY TYR LYS LYS VAL MET ALA THR ILE ASP SER PHE GLN SER PHE
ASN THR SER THR MET HIS PHE THR ASP GLU ARG ILE GLU TRP LYS ASP PRO ASP GLY MET LEU ARG ASP HIS ILE ASN ILE LEU
VAL THR LYS ASP ILE ASP PHE ASP ASN LEU GLY GLU ASN PRO CYS LYS ILE GLN LEU GLN THR SER SER ILE GLU GLY ALA TRP
15 GLY SER GLY VAL GLY PHE THR LEU THR CYS LEU VAL SER LEU THR ARG GLU CYS PRO THR PHE LEU THR SER ILE LYS ALA CYS
ASP LYS ALA ILE CYS TYR GLY ALA GLU SER VAL THR LEU THR ARG GLY GLN ASN THR VAL LYS VAL SER GLY LYS GLY GLY
HIS SER GLY SER THR PHE ARG CYS CYS HIS GLY GLU ASP CYS SER GLN ILE GLY LEU HIS ALA ALA ALA PRO HIS LEU ASP LYS
VAL ASN GLY ILE SER GLU ILE GLU ASN SER LYS VAL TYR ASP GLY ALA PRO GLN CYS GLY ILE LYS CYS TRP PHE VAL LYS
SER GLY GLU TRP ILE SER GLY ILE PHE SER GLY ASN TRP ILE VAL LEU LEU CYS VAL PHE LEU LEU PHE SER LEU VAL
20 LEU LEU SER ILE LEU CYS PRO VAL ARG LYS HIS LYS SER

FIG. 3

MET ALA THR MET GLU GLU LEU GLN ARG GLU LEU ASN ALA HIS GLU GLY GLN LEU VAL ILE ALA ALA ARG GLN LYS VAL ARG ASP
ALA GLU LYS GLN TYR GLU LYS ASP PRO ASP GLU LYS ASN LYS ARG THR LEU THR ASP ARG LEU ASN LYS ARG PRO THR LEU ASN LYS ARG GLU GLY VAL ALA VAL SER ILE

5 GLN ALA LYS ILE ASP GLU LYS LYS ARG GLN LEU ALA ASP ARG ILE ALA THR GLY LYS ASN LEU GLY LYS ASN LEU GLY LYS LYS GLU GLN ASP PRO THR
GLY VAL GLU PRO GLY ASP HIS LEU LYS GLU LYS GLY ARG SER MET LEU SER TYR GLY ASN VAL LEU ASN HIS LEU ASP ILE ASP ILE ASP
GLU PRO THR GLY GLN THR ALA ASP TRP LEU SER ILE ILE VAL TYR LEU THR SER PHE VAL VAL PRO ILE LEU LEU LYS ALA LEU
TYR MET LEU THR THR ARG GLY ARG GLN THR THR LYS ASP ASN LYS GLY THR ARG ILE ARG PHE LYS ASP ASP SER SER PHE GLU
ASP VAL ASN GLY ILE ARG LYS PRO LYS HIS LEU TYR VAL SER LEU PRO ASN ALA GLN SER SER MET LYS ALA GLU GLU ILE THR

10 PRO GLY ARG TYR ARG THR ALA VAL CYS GLY LEU TYR PRO ALA GLN ILE LYS ALA ARG GLN MET ILE SER PRO VAL MET SER
VAL ILE GLY PHE LEU ALA LEU ALA LYS ASP TRP SER ASP ARG ILE GLU GLN TRP LEU ILE GLU PRO CYS LYS LEU PRO ASP
THR ALA ALA VAL SER LEU GLY LEU GLY PRO ALA THR ASN ARG ASP TYR LEU ARG GLN ILE ARG GLN VAL ALA LEU GLY ASN MET
GLU THR LYS GLU SER LYS ALA ILE ARG GLN HIS ALA ALA ALA GLY CYS SER MET ILE GLU ASP ILE GLU SER PRO SER SER
ILE TRP VAL PHE ALA GLY ALA PRO ARG CYS PRO PRO THR CYS LEU PHE ILE ALA GLY ILE ALA GLU LEU GLY ALA PHE PHE

15 SER ILE LEU GLN ASP MET ARG ASN THR ILE MET ALA SER LYS THR VAL GLY THR SER GLU GLY LYS LEU ARG LYS LYS SER SER
PHE TYR GLN SER TYR LEU ARG ARG THR GLN SER MET GLY ILE GLN LEU GLY GLN ARG ILE ILE VAL LEU PHE MET VAL ALA
TRP GLY LYS GLU ALA VAL ASP ASN PHE HIS LEU GLY ASP MET ASP PRO GLU LEU ARG THR LEU ALA GLN SER LEU ILE ASP
VAL LYS VAL LYS GLU ILE SER ASN GLN GLU PRO LEU LYS LEU

FIG. 4-1

```
    ATG GGG ATA TGG AAG TGG CTA GTG ATG GCC AGT GTG ATG CCT GTT TTG ACA CTG AGA AAT GTC TAT GAC ATG AAA
    ATT GAG TGC CCC CAT ACA GTA AGT TTT GGG GAA AAC AGT GTG ATA GGT TAT GTA GAA TTA CCC CCC GTG CCA TTG GCC
5   GAC ACA GCA CAG ATG GTG CCT GAG AGT TCT TGT AAC ATG GAT AAT CAC CAA TCG TTG AAT ACA ATA AAA TAT ACC
    CAA GTA AGT TGG AGA GGA AAG GCT GAT CAG TCA CAG TCT AGT CAA AAT TCA TTT GAG AGA GTG TCC ACT GAA GTT GAC
    TTG AAA GGA ACA TGT GTT CTA AAA CAC AAA ATG GTG GAA GAA TCA TAC CGT AGT AGG AAA TCA GTA ACC TGT TAC GAC
    CTG TCT TGC AAT AGC ACT TAC TGC AAG GTG TTA GGA GTG GTT TAT GAG AGA AGT TAC TGT ATG ACA GGA GTC CTG ATT GAA
    TGT TTG ATT GCA TTG GGA CCA TAC AGR GTA CAG GTG GTT TAT GAG AGA AGT TAC TGT ATG ACA GGA GTC CTG ATT GTA
10  GGG AAA TGC TTT GTC CCA GAT CAA AGT GTG GTC AGT ATT ATC AAG CAT GGG ATC TTT GAT ATT GCA AGT TTT CAT ATT GTA
    TGT TTC TTT GTT GCA GTT AAA GGG AAT ACT TAT AAA ATT TTT GAA CAG GTT AAG AAA TCC TTT GAA TCA ACA TGC AAT GAT
    ACA GAG AAT AAA GTG CAA GGA TAT TAT ATT TGT ATT GTA GGG GGA AAC TCT GCA CCA ATA TAT GTT CCA ACA CTT GAT
    GAT TTC AGA TCC ATG GAA GCA TTT ACA GGA ATC TTC AGA TCA CCA CAT GGG GAA GAT CAT GAT CTG GCT GGA GAA GAA
    ATT GCA TCT TAT TCT ATA GTC GGA CCT GCC AAT GCA AAA GTT CCT CAT AGT GCT AGC TCA GAT ACA TTG AGC TTG ATT GCC
15  TAT TCA GGT ATA CCA TCT TAT TCT TCC CTT AGC ATC CTA ACA AGT TCA ACA GAA GCT AAG CAT GTA TTC AGC CCT GGG TTG
    TTC CCA AAA CTT AAT CAC ACA AAT TGT GAT AAA AGT GCC ATA CCA CTC ATA TGG ACT GGG ATG ATT GAT TTA CCT GGA
    TAC TAC GAA GCT GTC GTC CAC CCT TGT ACA GTT TTT TGC GTA GTT TTC GTA TTA TCA GGT CCT GGG GCA TCA TGT GAA GCC TTT TCT GAA GGC
    GGG ATT TTC AAC ATA ACC TCT CCC ATG TGC TTA GTG TCA AAA CAA AAT CGA TTC CGG TTA ACA GAA CAA CAG CAA GTG AAT
    TTT GTG TGT CAG CGA GTG GAC ATG GAC ATT GTT GTG TAC TGC AAC GGG CAG AGG AAA GTA ATA TTA ACA AAA ACT CTA
20  GTT ATT GGA CAG TGT ATA TAT ACT ATA ACA AGC TTA XXX TCA TTA CTA CCT GGA GTA GCA CAT TCT ATT GCT GTT GAA TTG
```

FIG. 4-2

```
TGT GTA CCT GGG TTC CAT GGT TGG GCC ACA GCT GCT CTG CTT GTT ACA TTC TGT TTC GGA TGG GTT CTT ATA CCA GCA ATT
ACA TTT ATC ATA CTA ACA GTC CTA AAG TTC ATT GCT AAT AAT TTT CAC ACA AGT AAT CAA GAG AAT AGG CTA AAA TCA
GTA CTT AGA AAG ATA AAG GAA GAG TTT GAA AAA ACA AAA GGC TCA ATG GTA TGT GAT GTC TGC AAG TAT GAG TGT GAA
ACA TAT AAA GAA TTA AAG GCA CAC GGG GTA TCA TGC CCC CAA TCT CAA GTT CCT TAC TGT TTT ACT CAT TGT GAA CCT ACA
25 GAA GCA GCA TTC CCA GTC CAT TAC AAG GTA TGC CAA GTT ACT CAC AGA TTC AGG GAT GAT CTA AAG AAA ACT GTT ACT
CCT CAA AAT TTT ACA CCA GGA TGT TAC CGG ACA CTA AAT TTA AGA TAC AAA AGC AGG TGC TAC ATC TTT ACA ATG TGG
ATA TTT CTT GTC TTA GAA TCC ATA CTG TGG GCT GCA AGT GCA TCA GAG ACA CCA TTA ACT CCT GTC TGG AAT GAC AAT
GCC CAT GGG GTA GGT TCT GTT CCT ATG CAT ACA GAT TTA GAG CTT GAT TTC TCT TTA ACA TCC AGT TCC AAG TAT ACA TAC
CGT AGG AAG TTA ACA ACC CCA CTT GAG GAA GCA CAA TCC ATT GAC CTA CAT ATT GAA ATA GAA GAA CAG ACA ATT GGT
30 GTT GAT GTG CAT GCT CTA GGA CAC TGG TTT GAT GGT CGT CTT AAC CTT AAA ACA TCC TTT CAC TGT TAT GGT GCT TGT ACA
AAG TAT GAA TAC CCT TGG CAT ACT GCA AAG TGC CAT TAT GAA AGA GAT TAC CAA TAT GAA ACG AGC TGG GGT TGT AAT
CCA TCA GAT TGT CCT GGG GTG GGC ACA GGC TGT ACA GCA TGT GGT TTA TAC CTA GAT CAA CTG AAA CCA GTT GGT AGT
GCT TAT AAA ATT ATC ACA ATA AGG TAC AGC AGG AGA GTC TGT GTT CAG TTT GGG GAG GAA AAC CTT TGT AAG ATA ATA
GAG ATG AAT GAT TGT TTT GTA TCT AGG CAT GTT AAG GTC TGC ATA ATT GGT ACA GTA TCT AAA TTC TCT CAG GGT GAT ACC
```

FIG. 4-3

```
35  TTA TTG TTT TTT GGA CCG CTT GAA GGT GGT CTA ATA TTT AAA CAC TGG TGT ACA TCC ACA TGT CAA TTT GGT GAC CCA
    GGA GAT ATC ATG AGT CCA AGA GAC AAA GGT TTT TTA TGC CCT GAG TTT CCA GGT AGT TTC AGG AAG AAA TGC AAC TTT
    GCT ACT ACC CCT ATT TGT GAG TAT GAT GGA AAT ATG GTC TCA GGT TAC AAG AAA GTG ATG GCG ACA ATT GAT TCC TTC CAA
    TCT TTT AAT ACA AGC ACT ATG CAC TTC ACT GAT GAA AGG ATA GAG TGG AAA GAC CCT GAT GGA ATG CTA AGG GAC CAT
    ATA AAC ATT TTA GTA ACG AAG GAC ATT GAC TTT GAT AAC CTT GGT GAA AAT CCT TGC AAA ATT GGC CTA CAA ACA TCT
40  TCT ATT GAG GGG GCC TGG GCT TGT GGT TCT GGT GTG GGG TTC ACA ATA ACA TGT CTG GTA TCA CTA ACA GAA TGT CCT ACC TTT TTG
    ACC TCA ATA AAG GCT TGT GAT AAG GCT ATC TGT TAT GGT GCA GAG AGT GTA ACA TTG ACA AGA GGA CAA AAT ACA GTC
    AAG GTA TCA GGG AAA GGT GGC CAT AGT GGT TCA ACA TTT AGG TGT TGC CAT GGG GAG GAC TGT TCA CAA ATT GGA CTC
    CAT GCT GCT GCA CCT CAC CTT GAC AAG GTA AAT GGG ATT TCT GAG ATA GAA AAT AGT AAA GTA TAT GAT GAT GGG GCA
    CCG CAA TGT GGG ATA AAA TGT TGG TTT GTT AAA TCA GGG GAA TGG ATT TCA GGG ATA TTC AGT GGT AAT TGG ATT GTA
45  CTC ATT GTC CTC TGT GTA TTT CTA TTG TTC TCC TTG GTT TTA CTA AGC ATT CTC TGT CCC GTA AGG AAG CAT AAA AAA TCA
    TAG
```

FIG. 5

```
ATG GCA ACT ATG GAG GAA TTA CAG AGG GAA ATC AAT GCC CAT GAG GGT CAA TTA GTG ATA GCC AGG CAG AAG GTG AGG
GAT GCA GAA AAA CAG TAT GAA AAG GAT CCA GAT GAG TTG AAC AAG AGA ACA TTA ACT GAC CGA GAG GGC GTT GCA GTA
TCT ATC CAG GCA AAA ATT GAT GAG TTA AAA AGG CAA CTG GCA GAT AGG ATT GCA ACT GGG AAA AAC CTT GGG AAG GAA
CAA GAT CCA ACA GGG GTG GAG CCT GGA GAC CAT CTG AAA GAG AGG TCA ATG GAG CTC AGT GT TAT GGT AAT GTG CTG GAT TTA
AAC CAT TTG GAT ATT GAT GAA CCT ACA GGA CAG ACA GCA GAC TGG CTG AGC ATC ATC GTC TAT CTT ACA TCC TTT GTC GTC
CCG ATA CTT CTG AAA GTC CTG TAT ATG TTG ACA ACA AGG GGG AGG CAA ACT ACC AAG GAT AAT AAA GGG ACC CGG ATT
CGA TTT AAG GAT GAT AGC TCG TTC GAG GAT GTT AAC GGT ATC CGG AAA CCA AAA CAT CTT TAC GTG TCC TTG CCA AAT
GCA CAG TCA AGC ATG AAG GCA GAA GAG ATT ACA CCT GGT AGA TAT AGA ACA GCA GTC TGT GGG CTC TAC CCT GCA CAG
ATT AAG GCA CGG CAG ATG ATC AGT GGT ATG AGT GTA ATT GGT TTT CTA GCA TTA GCA AAG GAC TGG AGT GAT CGT
ATC GAA CAA TGG TTA ATT GAA CCT TGC AAG CTT CTT CCA GAT ACA GCA GCA GTT AGC CTC CTC GGT GGT CCT GCA ACA
AAC AGG GAC TAC TTA CGG CAG CGG CAA GTG GCA TTA GGC AAT ATG GAG ACA AAG GAG TCA AAG GCT ATA CGC CAG CAT
GCA GAA GCA GCT GGC TGT AGC GCT ATG ATT GAA GAT ATT GAG TCA CCA TCA TCA ATA TGG GTT TTT GCT GGA GCA CCA GAC
CGT TGT CCA CCA ACA TGT TTG TTT ATA GCA GGT ATT GCT GAG CTT GGG GCA TTT TTT CCA TC CTG CAG GAC ATG CGA AAT
ACA ATC ATG GCA TCT AAG ACR GTT GGA ACA TCT GAG GAG AAG CTA CGG AAG AAA TCA TCA TTT TAT CAG TCC TAC CTC
AGA AGG ACA CAA TCA ATG GGG ATA CAA CTA GGC CAG AGA ATT GTG CTC TTC ATG GTT GCC TGG GGA AAG GAG GCT
GTG GAC AAC TTC CAC TTA GGG GAT GAT ATG GAT CCT GAG CTA AGG ACA CTG GCA CAG AGC TTG ATT GAT GTC AAA GTG
AAG GAA ATC TCC AAC CAA GAG CCT TTG AAA CTC
```

HANTAVIRUS VACCINE

BACKGROUND OF THE INVENTION

This application is a continuation-in-part of U.S. Ser. No. 07/799,479, filed on Nov. 14, 1991, issuing as U.S. Pat. No. 5,298,423, hereby incorporated by reference.

Infectious febrile diseases with hemorrhagic and renal manifestations have been recognized across the Eurasian land mass for more than 50 years. Seven thousand cases of a "war nephritis" clinically similar to nephorpathia epidemica (NE) were reported among British soldiers stationed in Flanders during World War I. Brown, *Lancet i.*, 316–395 (1916). Nevertheless, these disorders were not given much attention by Western physicians until the early 1950's during the Korean conflict, when over 3000 cases were diagnosed among United Nations forces. Earle, *Am. J. Med.* 16: 617–709 (1954).

Subsequently, it was recognized that Korean hemorrhagic fever and clinically similar diseases, collectively termed hemorrhagic fever with renal syndrome (HFRS), pose a significant health threat in much of Asia and parts of Europe and Scandinavia. Non-pathogenic infection of rodent populations apparently provides a reservoir for the causative agent. Infection of humans occurs via aerosol of the agent, a Hantavirus of the family Bunyaviridae, from rodent urine, feces and saliva. Mortality rates have decreased from the 10 to 15% seen during the Korean conflict to 5% or less, if improved fluid and electrolyte management and/or renal dialysis are available. Currently, an estimated 50,000–100,000 case occur annually in the Peoples' Republic of China, with mortality rates ranging from 5 to 20%, in various provinces.

A recent randomized, placebo-controlled clinical trial of intravenous ribavirin in HFRS patients presenting within the first six days of clinical symptoms demonstrated a significant reduction in mortality. Huggins et al., *J. Infect. Dis.* 164: 1119–1127 (1991); Lee and Ahn, *J. Korean Soc. Virol.* 18: 143–148 (1988). Otherwise, management of all HFRS patients is highly individualized and focused on supportive care.

A Hantavirus vaccine has been approved and is in use in South Korea. Lee and Ahn (1988). This vaccine was developed by serial passage of the virus in brains of suckling pigs, followed by inactivation with formalin. Initial claims reported that two doses of the vaccine, given via a subcutaneous route one month apart, resulted in 100% seroconversion as measured by immunofluorescence. The production of this vaccine, however, was not in compliance with current U.S. Food and Drug Administration guidelines on "Good Manufacturing Practices," and the protective efficacy has not yet been determined. Furthermore, adventitious agents in the product were not rigorously excluded and the animal colony used for the vaccine's development was not pathogen-free. Other vaccines are currently undergoing testing in Japan, North and South Korea and China. Both Korean vaccine trials involved the use of formalin-inactivated, Hantaan virus-infected mouse brain. Suh et al., *Virus Information Exchg. Newsl.* 6: 131 (1989); Lee and Ahn (1988). The Chinese and Japanese trials involve inactivated, tissue culture-derived Hantavirus preparations. Yu and Zhe, *Virus Information Exchg. Newsl.* 6: 131 (1989).

"Hantaan" virus, the etiologic agent of Korean hemorrhagic fever, was originally isolated from the Korean striped field mouse. Lee et al., *J. Infect. Dis.* 137: 298–307 (1978). This serotype is the prototype for the Hantavirus genus. Schmaljohn and Dalrymple, *Virology* 131: 482–491 (1983). Hantaan virus particles contain three major structural proteins: the nucleocapsid or "N" protein and the "G1" and "G2" glycoproteins. Id. In addition, virions contain an RNA-dependent RNA polymerase function. Id. Like other members of the Bunyaviridae family, the viral genome is comprised of three RNA segments: small (S), middle (M) and large (L). Id.

More detailed examination of the molecular structure of Hantaan virus was provided following cloning and sequencing of cDNA's for the S and M segments. In their 1986 paper, Schmaljohn et al. reported that unlike other Bunyadviridae, the 1696 nucleotide Hantaan virus S segment did not code for a non-structural protein (NS). Schmaljohn et al., *Virology* 155: 633–643 (1986). Rather, they found a single open reading frame encoding a putative 428 amino acid polypeptide, presumed to be the N protein, a result consistent with earlier data from cell-free translation studies. Id. The cDNA for the N product is disclosed and claimed in U.S. Pat. No. 5,298,423.

In 1987, Schmaljohn et al. reported the 3616 base nucleotide sequence for the Hantaan virus M segment. Within this region, a single open reading frame encoding 1135 amino acids was found. Schmaljohn et al., *Virology* 157: 31–39 (1987). Amino-terminal sequence of the G1 and G2 glycoproteins demonstrated that this single open reading frame coded for both glycoproteins (5'-G1-G2-3'), probably expressed in the form of a polyprotein precursor that is cleaved post- or cotranslationally, both to separate the two glycoproteins and to remove the amino-terminal 17 amino acids of the G1 glycoprotein. Id. These data were confirmed later the same year by a different group. Yoo and Kang, *Nuc. Acids Res.* 15: 6299–6300 (1987). The cDNA's for the G1 and G2 products are disclosed and claimed in U.S. Pat. No. 5,298,423.

A second Hantavirus, the "Seoul" serotype, has been isolated and sequenced. Antic et al., *Virus Res.* 19: 47–58 (1991): Antic et al., *Virus Res.* 19: 59–66 (1991). The Hantaan and Seoul serotypes show about 75% sequence homology at the RNA level. Antic et al., *Virus Res.* 24: 35–46 (1992). Patients with HFRS caused by the Seoul serotype appear to suffer a milder clinical form of the disease. Recent studies indicate that six other Hantaviruses exist: Puumala, Prospect Hill, Thailand, Dobrava, Thottapalayam and Four Corners. Arikawa et al., *Virology* 176: 114–125 (1990); Xiao et al., *Virology* 198: 205–217 (1994); Chu et al., *Virology* 198: 196–204 (1994); Nichol et al., "Genetic Identification of a Novel Hantavirus Associated with an Outbreak of Acute Respiratory Illness in the Southwestern United States, " Science in press (1994). Only Hantaan, Seoul, Puumala , and Dobrava are known to cause HFRS. Four Corners was described recently and linked to an extremely deadly form of pulmonary distress in the southwest United States. Thottapalayam, Prospect Hill and Thailand are not known to cause human disease.

In 1988, the first use of a recombinant Hantavirus antigen as a diagnostic agent was reported. Schmaljohn et al., *J. Gen. Virol.* 69: 777–786 (1988). cDNA's corresponding to the S segment were used in a Baculovirus expression system, and the resulting N polypeptide showed specific reactivity with immune sera from rabbits, rats and humans or Hantaan virus-specific monoclonal antibodies. Id. These data were extended and confirmed in a second study, also involving a recombinant, Baculovirus-expressed N protein. Rossi et al., *Arch. Virol.* S1: 19–28 (1990). Together, these reports proved that recombinant Hantavirus proteins could serve effectively as diagnostic reagents in screening for Hantavirus infection.

Having confirmed that recombinantly-produced Hantavirus antigens were immunologically related to those produced by Hantavirus infection, researchers next sought to determine whether such antigens might be used as a vaccine to protect animals against infection by Hantavirus. In one such study, immunization with a vaccinia virus vectors expressing Hantaan virus glycoproteins not only elicited antibody responses to Hantaan virus antigens in mice, they also protected hamsters from Hantaan virus infection, as measured by indirect immunofluorescence of lung and kidney tissue. Schmaljohn et al., *J. Virol.* 64: 3162–3170 (1990). While promising, these data were deemed only to "demonstrate the feasibility of using expressed Hantaan virus proteins to immunize animals to Hantaan virus" and "should provide a basis for future exploitation of recombinant-expressed Hantaan virus proteins as potential human vaccines." Id. at page 3170.

A later report by Schamljohn et al. reported the development of a different vaccinia-based vaccine containing both the M and S segments of Hantaan virus. Schmaljohn et al., *Vaccine* 10: 10–13 (1992). In Dec. 1992, preliminary immunization data for the M+S vaccinia virus vaccine was presented at a meeting in India. There, it was shown that the M+S vaccine protected 3 out of 4 hamsters after a single immunization and 4 out of 4 hamsters given a secondary immunization. These data were admitted to be of no statistical relevance and "repeat preclinical experiments . . . with this potential human product" were reportedly in progress.

Even though mortality rates for HFRS have dropped over the past several decades, this syndrome still represents a significant threat to populations around the world, especially those in regions where high quality supportive care is not readily available. Therefore, it remains of utmost importance to develop a safe and effective vaccine against Hantavirus. Currently, no vaccines have been demonstrated to meet both of these criteria.

SUMMARY OF THE INVENTION

It is, therefore, an object of this invention to provide a vaccine, suitable for use in humans, that is capable of inducing a protective immune response specific for Hantavirus. In addition, it is an object of the invention to provide specific methodology for the safe and effective implementation of such a vaccine.

In satisfying the foregoing objective, there is provided a vaccine formulation suitable for use in a human, comprising:
(i) infectious vaccinia virus that comprises a polynucleotide encoding
   (a) the Hantavirus polypeptides designated N, G1 and G2 (SEQ ID NOS 3, 1 and 2 respectively), and
   (b) all vaccinia virus polypeptides necessary for replication of said virus in a cell derived from said human, but not a functional thymidine kinase; and
(ii) a pharmaceutically-acceptable carrier, excipient or diluent, wherein said vaccine formulation comprises a single dose of $1\times10^5$ to $7\times10^7$ plaque-forming units of vaccinia virus.

In addition, there is provide a method for inducing a Hantavirus-protective immune response in a human, comprising the steps of:
(i) providing a vaccine formulation suitable for use in a human comprising
   (a) infectious vaccinia virus activity and comprising a polynucleotide encoding
      (1) the Hantavirus polypeptides designated N, G1 and G2 (SEQ ID NOS 3, 1 and 2 respectively), and
      (2) all vaccinia virus polypeptides necessary for replication of said virus in a cell derived from said human, but not a functional thymidine kinase; and
   (b) a pharmaceutically-acceptable carrier, excipient or diluent,
(ii) administering said vaccine formulation to said human, wherein said vaccine formulation comprises a single dose of $1\times10^5$ to $7\times10^7$ plaque-forming units of vaccinia virus.

In a preferred embodiment, the expression of vaccine encoded polypeptides is under control of the vaccinia virus 11 kD promoter.

In another preferred emobidment, the Hantavirus polypeptides are derived from the Hantaan serotype. Preferred sequences in this regard are the G1 sequence (SEQ 10 NO: 1):

MET GLY ILE TRP LYS TRP LEU VAL MET ALA SER LEU VAL TRP PRO VAL LEU THR LEU ARG ASN VAL TYR

ASP MET LYS ILE GLU CYS PRO HIS THR VAL SER PHE GLY GLU ASN SER VAL ILE GLY TYR VAL GLU LEU

PRO PRO VAL PRO LEU ALA ASP THR ALA GLN MET VAL PRO GLU SER SER CYS ASN MET ASP ASN HIS GLN

SER LEU ASN THR ILE THR LYS TYR THR GLN VAL SER TRP ARG GLY LYS ALA ASP GLN SER GLN SER SER

GLN ASN SER PHE GLU THR VAL SER THR GLU VAL ASP LEU LYS GLY THR CYS VAL LEU LYS HIS LYS MET

VAL GLU GLU SER TYR ARG SER ARG LYS SER VAL THR CYS TYR ASP LEU SER CYS ASN SER THR TYR CYS

LYS PRO THR LEU TYR MET ILE VAL PRO ILE HIS ALA CYS ASN MET LYS SER CYS LEU ILE ALA LEU GLY

PRO TYR ARG VAL GLN VAL VAL TYR GLU ARG SER TYR CYS MET THR GLY VAL LEU ILE GLU GLY LYS CYS

PHE VAL PRO ASP GLN SER VAL VAL SER ILE ILE LYS HIS GLY ILE PHE ASP ILE ALA SER VAL HIS ILE VAL

CYS PHE PHE VAL ALA VAL LYS GLY ASN THR TYR LYS ILE PHE GLU GLN VAL LYS LYS SER PHE GLU SER

THR CYS ASN ASP THR GLU ASN LYS VAL GLN GLY TYR TYR ILE CYS ILE VAL GLY ASN SER ALA PRO ILE

TYR VAL PRO THR LEU ASP ASP PHE ARG SER MET GLU ALA PHE THR GLY ILE PHE ARG SER PRO HIS GLY

GLU ASP HIS ASP LEU ALA GLY GLU GLU ILE ALA SER TYR SER ILE VAL GLY PRO ALA ASN ALA LYS VAL

PRO HIS SER ALA SER SER ASP THR LEU SER LEU ILE ALA TYR SER GLY ILE PRO SER TYR SER SER LEU SER

-continued

ILE LEU THR SER SER THR GLU ALA LYS HIS VAL PHE SER PRO GLY LEU PHE PRO LYS LEU ASN HIS THR ASN

CYS ASP LYS SER ALA ILE PRO LEU ILE TRP THR GLY MET ILE ASP LEU PRO GLY TYR TYR GLU ALA VAL HIS

PRO CYS THR VAL PHE CYS VAL LEU SER GLY PRO GLY ALA SER CYS GLU ALA PHE SER GLU GLY GLY ILE

PHE ASN ILE THR SER PRO MET CYS LEU VAL SER LYS GLN ASN ARG PHE ARG LEU THR GLU GLN GLN VAL

ASN PHE VAL CYS GLN ARG VAL ASP MET ASP ILE VAL VAL TYR CYS ASN GLY GLN ARG LYS VAL ILE LEU

THR LYS THR LEU VAL ILE GLY GLN CYS ILE TYR THR ILE THR SER LEU PHE SER LEU LEU PRO GLY VAL

ALA HIS SER ILE ALA VAL GLU LEU CYS VAL PRO GLY PHE HIS GLY TRP ALA THR ALA ALA LEU LEU VAL

THR PHE CYS PHE GLY TRP VAL LEU ILE PRO ALA ILE THR PHE ILE ILE LEU THR VAL LEU LYS PHE ILE ALA

ASN ILE PHE HIS THR SER ASN GLN GLU ASN ARG LEU LYS SER VAL LEU ARG LYS ILE LYS GLU GLU PHE

GLU LYS THR LYS GLY SER MET VAL CYS ASP VAL CYS LYS TYR GLU CYS GLU THR TYR LYS GLU LEU LYS

ALA HIS GLY VAL SER CYS PRO GLN SER GLN CYS PRO TYR CYS PHE THR HIS CYS GLU PRO THR GLU ALA

ALA PHE GLN ALA HIS TYR LYS VAL CYS GLN VAL THR HIS ARG PHE ARG ASP ASP LEU LYS LYS THR VAL

THR PRO GLN ASN PHE THR PRO GLY CYS TYR ARG THR LEU ASN LEU PHE ARG TYR LYS SER ARG CYS TYR

ILE PHE THR MET TRP ILE PHE LEU LEU VAL LEU GLU SER ILE LEU TRP ALA ALA SER ALA the G2 sequence (SEQ ID NO: 2):

SER GLU THR PRO LEU THR PRO VAL TRP ASN ASP ASN ALA HIS GLY VAL GLY SER VAL PRO MET HIS THR

ASP LEU GLU LEU ASP PHE SER LEU THR SER SER SER LYS TYR THR TYR ARG ARG LYS LEU THR ASN PRO

LEU GLU GLU ALA GLN SER ILE ASP LEU HIS ILE GLU ILE GLU GLU GLN THR ILE GLY VAL ASP VAL HIS ALA

LEU GLY HIS TRP PHE ASP GLY ARG LEU ASN LEU LYS THR SER PHE HIS CYS TYR GLY ALA CYS THR LYS

TYR GLU TYR PRO TRP HIS THR ALA LYS CYS HIS TYR GLU ARG ASP TYR GLN TYR GLU THR SER TRP GLY

CYS ASN PRO SER ASP CYS PRO GLY VAL GLY THR GLY CYS THR ALA CYS GLY LEU TRY LEU ASP GLN LEU

LYS PRO VAL GLY SER ALA TYR LYS ILE ILE THR ILE ARG TYR SER ARG ARG VAL CYS VAL GLN PHE GLY

GLU GLU ASN LEU CYS LYS ILE ILE ASP MET ASN ASP CYS PHE VAL SER ARG HIS VAL LYS VAL CYS ILE ILE

GLY THR VAL SER LYS PHE SER GLN GLY ASP THR LEU LEU PHE PHE GLY PRO LEU GLU GLY GLY GLY LEU

ILE PHE LYS HIS TRP CYS THR SER THR CYS GLN PHE GLY ASP PRO GLY ASP ILE MET SER PRO ARG ASP LYS

GLY PHE LEU CYS PRO GLU PHE PRO GLY SER PHE ARG LYS LYS CYS ASN PHE ALA THR THR PRO ILE CYS

GLU TYR ASP GLY ASN MET VAL SER GLY TYR LYS LYS VAL MET ALA THR ILE ASP SER PHE GLN SER PHE

ASN THR SER THR MET HIS PHE THR ASP GLU ARG ILE GLU TRP LYS ASP PRO ASP GLY MET LEU ARG ASP

HIS ILE ASN ILE LEU VAL THR LYS ASP ILE ASP PHE ASP ASN LEU GLY GLU ASN PRO CYS LYS ILE GLY LEU

GLN THR SER SER ILE GLU GLY ALA TRP GLY SER GLY VAL GLY PHE THR LEU THR CYS LEU VAL SER LEU

THR GLU CYS PRO THR PHE LEU THR SER ILE LYS ALA CYS ASP LYS ALA ILE CYS TYR GLY ALA GLU SER

VAL THR LEU THR ARG GLY GLN ASN THR VAL LYS VAL SER GLY LYS GLY GLY HIS SER GLY SER THR PHE

ARG CYS CYS HIS GLY GLU ASP CYS SER GLN ILE GLY LEU HIS ALA ALA ALA PRO HIS LEU ASP LYS VAL ASN

GLY ILE SER GLU ILE GLU ASN SER LYS VAL TYR ASP ASP GLY ALA PRO GLN CYS GLY ILE LYS CYS TRP PHE

VAL LYS SER GLY GLU TRP ILE SER GLY ILE PHE SER GLY ASN TRP ILE VAL LEU ILE VAL LEU CYS VAL PHE

LEU LEU PHE SER LEU VAL LEU LEU SER ILE LEU CYS PRO VAL ARG LYS HIS LYS LYS SER and the N sequence (SEQ ID NO: 3):

MET ALA THR MET GLU GLU LEU GLN ARG GLU ILE ASN ALA HIS GLU GLY GLN LEU VAL ILE ALA ARG GLN

LYS VAL ARG ASP ALA GLU LYS GLN TYR GLU LYS ASP PRO ASP GLU LEU ASN LYS ARG THR LEU THR ASP

ARG GLU GLY VAL ALA VAL SER ILE GLN ALA LYS ILE ASP GLU LEU LYS ARG GLN LEU ALA ASP ARG ILE ALA THR GLY LYS ASN LEU GLY LYS GLU GLN ASP PRO THR GLY VAL GLU PRO GLY ASP HIS LEU LYS GLU ARG SER MET LEU SER TYR GLY ASN VAL LEU ASP LEU ASN HIS LEU ASP ILE ASP GLU PRO THR GLY GLN THR ALA ASP TRP LEU SER ILE ILE VAL TYR LEU THR SER PHE VAL VAL PRO ILE LEU LEU LYS ALA LEU TYR MET LEU THR THR ARG GLY ARG GLN THR THR LYS ASP ASN LYS GLY THR ARG ILE ARG PHE LYS ASP ASP SER SER PHE GLU ASP VAL ASN GLY ILE ARG LYS PRO LYS HIS LEU TYR VAL SER LEU PRO ASN ALA GLN SER SER MET LYS ALA GLU GLU ILE THR PRO GLY ARG TYR ARG THR ALA VAL CYS GLY LEU TYR PRO ALA GLN ILE LYS ALA ARG GLN MET ILE SER PRO VAL MET SER VAL ILE GLY PHE LEU ALA LEU ALA LYS ASP TRP SER ASP ARG ILE GLU GLN TRP LEU ILE GLU PRO CYS LYS LEU LEU PRO ASP THR ALA ALA VAL SER LEU LEU GLY GLY PRO ALA THR ASN ARG ASP TYR LEU ARG GLN ARG GLN VAL ALA LEU GLY ASN MET GLU THR LYS GLU SER LYS ALA ILE ARG GLN HIS ALA GLU ALA ALA GLY CYS SER MET ILE GLU ASP ILE GLU SER PRO SER SER ILE TRP VAL PHE ALA GLY ALA PRO ASP ARG CYS PRO PRO THR CYS LEU PHE ILE ALA GLY ILE ALA GLU LEU GLY ALA PHE PHE SER ILE LEU GLN ASP MET ARG ASN THR ILE MET ALA SER LYS THR VAL GLY THR SER GLU GLU LYS LEU ARG LYS LYS SER SER PHE TYR GLN SER TYR LEU ARG ARG THR GLN SER MET GLY ILE GLN LEU GLY GLN ARG ILE ILE VAL LEU PHE MET VAL ALA TRP GLY LYS GLU ALA VAL ASP ASN PHE HIS LEU GLY ASP ASP MET ASP PRO GLU LEU ARG THR LEU ALA GLN SER LEU ILE ASP VAL LYS VAL LYS GLU ILE SER ASN GLN GLU PRO LEU LYS LEU, of which the first 17 amino acids of G1 are apparently cleaved to form the mature G1 protein and, therefore, are optional.

The preferred coding sequence for the G1, G2 and N polypeptides is (SEQ ID NO: 4):

ATG GGG ATA TGG AAG TGG CTA GTG ATG GCC AGT TTA GTA TGG CCT GTT TTG ACA CTG AGA AAT GTC

TAT GAC ATG AAA ATT GAG TGC CCC CAT ACA GTA AGT TTT GGG GAA AAC AGT GTG ATA GGT TAT GTA

GAA TTA CCC CCC GTG CCA TTG GCC GAC ACA GCA CAG ATG GTG CCT GAG AGT TCT TGT AAC ATG GAT

AAT CAC CAA TCG TTG AAT ACA ATA ACA AAA TAT ACC CAA GTA AGT TGG AGA GGA AAG GCT GAT CAG

TCA CAG TCT AGT CAA AAT TCA TTT GAG AGA GTG TCC ACT GAA GTT GAC TTG AAA GGA ACA TGT GTT

CTA AAA CAC AAA ATG GTG GAA GAA TCA TAC CGT AGT AGG AAA TCA GTA ACC TGT TAC GAC CTG TCT

TGC AAT AGC ACT TAC TGC AAG CCA ACA CTA TAC ATG ATT GTA CCA ATT CAT GCA TGC AAT ATG ATG

AAA AGC TGT TTG ATT GCA TTG GGA CCA TAC AGR GTA CAG GTG GTT TAT GAG AGA GTA CTG TAT GCA

ACA GGA GTC CTG ATT GAA GGG AAA TGC TTT GTC CCA GAT CAA AGT GTG GTC AGT ATT ATC AAG CAT

GGG ATC TTT GAT ATT GCA AGT TTT CAT ATT GTA TGT TTC TTT GTT GCA GTT AAA GGG AAT ACT TAT AAA

ATT TTT GAA CAG GTT AAG AAA TCC TTT GAA TCA ACA TGC AAT GAT ACA GAG AAT AAA GTG CAA GGA

TAT TAT ATT TGT ATT GTA GGG GGA AAC TCT GCA CCA ATA TAT GTT CCA ACA CTT GAT GAT TTC AGA

TCC ATG GAA GCA TTT ACA GGA ATC TTC AGA TCA CCA CAT GGG GAA GAT CAT GAT CTG GCT GGA GAA

GAA ATT GCA TCT TAT TCT ATA GTC GGA CCT GCC AAT GCA AAA GTT CCT CAT AGT GCT AGC TCA GAT

ACA TTG AGC TTG ATT GCC TAT TCA GGT ATA CCA TCT TAT TCT TCC CTT AGC ATC CTA ACA AGT TCA ACA

GAA GCT AAG CAT GTA TTC AGC CCT GGG TTG TTC CCA AAA CTT AAT CAC ACA AAT TGT GAT AAA AGT

GCC ATA CCA CTC ATA TGG ACT GGG ATG ATT GAT TTA CCT GGA TAC TAC GAA GCT GTC CAC CCT TGT

ACA GTT TTT TGC GTA TTA TCA GGT CCT GGG GCA TCA TGT GAA GCC TTT CTT GAA GGC GGG ATT TTC

AAC ATA ACC TCT CCC ATG TGC TTA GTG TCA AAA CAA AAT CGA TTC CGG TTA ACA GAA CAG CAA GTG

AAT TTT GTG TGT CAG CGA GTG GAC ATG GAC ATT GTT GTG TAC TGA AAC GGG CAG AGG AAA GTA ATA

TTA ACA AAA ACT CTA GTT ATT GGA CAG TGT ATA TAT ACT ATA ACA AGC TTA XXX TCA TTA CTA CCT
GGA GTA GCA CAT TCT ATT GCT GTT GAA TTG TGT GTA CCT GGG TTC CAT GGT TGG GCC ACA GCT GCT
CTG CTT GTT ACA TTC TGT TTC GGA TGG GTT CTT ATA CCA GCA ATT ACA TTT ATC ATA CTA ACA GTC CTA
AAG TTC ATT GCT AAT AAT TTT CAC ACA AGT AAT CAA GAG AAT AGG CTA AAA TCA GTA CTT AGA AAG
ATA AAG GAA GAG TTT GAA AAA ACA AAA GGC TCA ATG GTA TGT GAT GTC TGC AAG TAT GAG TGT GAA
ACA TAT AAA GAA TTA AAG GCA CAC GGG GTA TCA TGC CCC CAA TCT CAA TGT CCT TAC TGT TTT ACT
CAT TGT GAA CCT ACA GAA GCA GCA TTC CCA GTC CAT TAC AAG GTA TGC CAA GTT ACT CAC AGA TTC
AGG GAT GAT CTA AAG AAA ACT GTT ACT CCT CAA AAT TTT ACA CCA GGA TGT TAC CGG ACA CTA AAT
TTA TTT AGA TAC AAA AGC AGG TGC TAC ATC TTT ACA ATG TGG ATA TTT CTT CTT GTC TTA GAA TCC ATA
CTG TGG GCT GCA AGT GCA TCA GAG ACA CCA TTA ACT CCT GTC TGG AAT GAC AAT GCC CAT GGG GTA
GGT TCT GTT CCT ATG CAT ACA GAT TTA GAG CTT GAT TTC TCT TTA ACA TCC AGT TCC AAG TAT ACA TAC
CGT AGG AAG TTA ACA AAC CCA CTT GAG GAA GCA CAA TCC ATT GAC CTA CAT ATT GAA ATA GAA GAA
CAG ACA ATT GGT GTT GAT GTG CAT GCT CTA GGA CAC TGG TTT GAT GGT CGT CTT AAC CTT AAA ACA
TCC TTT CAC TGT TAT GGT GCT TGT ACA AAG TAT GAA TAC CCT TGG CAT ACT GCA AAG TGC CAT TAT
GAA AGA GAT TAC CAA TAT GAA ACG AGC TGG GGT TGT AAT CCA TCA GAT TGT CCT GGG GTG GGC ACA
GGC TGT ACA GCA TGT GGT TTA TAC CTA GAT CAA CTG AAA CCA GTT GGT AGT GCT TAT AAA ATT ATC
ACA ATA AGG TAC AGC AGG AGA GTC TGT GTT CAG TTT GGG GAG GAA AAC CTT TGT AAG ATA ATA GAG
ATG AAT GAT TGT TTT GTA TCT AGG CAT GTT AAG GTC TGC ATA ATT GGT ACA GTA TCT AAA TTC TCT CAG
GGT GAT ACC TTA TTG TTT TTT GGA CCG CTT GAA GGT GGT GGT CTA ATA TTT AAA CAC TGG TGT ACA
TCC ACA TGT CAA TTT GGT GAC CCA GGA GAT ATC ATG AGT CCA AGA GAC AAA GGT TTT TTA TGC CCT
GAG TTT CCA GGT AGT TTC AGG AAG AAA TGC AAC TTT GCT ACT ACC CCT ATT TGT GAG TAT GAT GGA
AAT ATG GTC TCA GGT TAC AAG AAA GTG ATG GCG ACA ATT GAT TCC TTC CAA TCT TTT AAT ACA AGC
ACT ATG CAC TTC ACT GAT GAA AGG ATA GAG TGG AAA GAC CCT GAT GGA ATG CTA AGG GAC CAT ATA
AAC ATT TTA GTA ACG AAG GAC ATT GAC TTT GAT AAC CTT GGT GAA AAT CCT TGC AAA ATT GGC CTA
CAA ACA TCT TCT ATT GAG GGG GCC TGG GGT TCT GGT GTG GGG TTC ACA TTA ACA TGT CTG GTA TCA
CTA ACA GAA TGT CCT ACC TTT TTG ACC TCA ATA AAG GCT TGT GAT AAG GCT ATC TGT TAT GGT GCA
GAG AGT GTA ACA TTG ACA AGA GGA CAA AAT ACA GTC AAG GTA TCA GGG AAA GGT GGC CAT AGT GGT
TCA ACA TTT AGG TGT TGC CAT GGG GAG GAC TGT TCA CAA ATT GGA CTC CAT GCT GCT GCA CCT CAC
CTT GAC AAG GTA AAT GGG ATT TCT GAG ATA GAA AAT AGT AAA GTA TAT GAT GAT GGG GCA CCG CAA
TGT GGG ATA AAA TGT TGG TTT GTT AAA TCA GGG GAA TGG ATT TCA GGG ATA TTC AGT GGT AAT TGG
ATT GTA CTC ATT GTC CTC TGT GTA TTT CTA TTG TTC TCC TTG GTT TTA CTA AGC ATT CTC TGT CCC GTA
AGG AAG CAT AAA AAA TCA and (SEQ ID NO: 5)

ATG GCA ACT ATG GAG GAA TTA CAG AGG GAA ATC AAT GCC CAT GAG GGT CAA TTA GTG ATA GCC AGG
CAG AAG GTG AGG GAT GCA GAA AAA CAG TAT GAA AAG GAT CCA GAT GAG TTG AAC AAG AGA ACA TTA
ACT GAC CGA GAG GGC GTT GCA GTA TCT ATC CAG GCA AAA ATT GAT GAG TTA AAA AGG CAA CTG GCA
GAT AGG ATT GCA ACT GGG AAA AAC CTT GGG AAG GAA CAA GAT CCA ACA GGG GTG GAG CCT GGA GAC
CAT CTG AAA GAG AGG TCA ATG CTC AGT TAT GGT AAT GTG CTG GAT TTA AAC CAT TTG GAT ATT GAT
GAA CCT ACA GGA CAG ACA GCA GAC TGG CTG AGC ATC ATC GTC TAT CTT ACA TCC TTT GTC GTC CCG

-continued

```
ATA CTT CTG AAA GTC CTG TAT ATG TTG ACA ACA AGG GGG AGG CAA ACT ACC AAG GAT AAT AAA GGG

ACC CGG ATT CGA TTT AAG GAT GAT AGC TCG TTC GAG GAT GTT AAC GGT ATC CGG AAA CCA AAA CAT

CTT TAC GTG TCC TTG CCA AAT GCA CAG TCA AGC ATG AAG GCA GAA GAG ATT ACA CCT GGT AGA TAT

AGA ACA GCA GTC TGT GGG CTC TAC CCT GCA CAG ATT AAG GCA CGG CAG ATG ATC AGT CCA GTT ATG

AGT GTA ATT GGT TTT CTA GCA TTA GCA AAG GAC TGG AGT GAT CGT ATC GAA CAA TGG TTA ATT GAA

CCT TGC AAG CTT CTT CCA GAT ACA GCA GCA GTT AGC CTC CTC GGT GGT CCT GCA ACA AAC AGG GAC

TAC TTA CGG CAG CGG CAA GTG GCA TTA GGC AAT ATG GAG ACA AAG GAG TCA AAG GCT ATA CGC CAG

CAT GCA GAA GCA GCT GGC TGT AGC ATG ATT GAA GAT ATT GAG TCA CCA TCA TCA ATA TGG GTT TTT

GCT GGA GCA CCA GAC CGT TGT CCA CCA ACA TGT TTG TTT ATA GCA GGT ATT GCT GAG CTT GGG GCA

TTT TTT TCC ATC CTG CAG GAC ATG CGA AAT ACA ATC ATG GCA TCT AAG ACR GTT GGA ACA TCT GAG

GAG AAG CTA CGG AAG AAA TCA TCA TTT TAT CAG TCC TAC CTC AGA AGG ACA CAA TCA ATG GGG ATA

CAA CTA GGC CAG AGA ATT ATT GTG CTC TTC ATG GTT GCC TGG GGA AAG GAG GCT GTG GAC AAC TTC

CAC TTA GGG GAT GAT ATG GAT CCT GAG CTA AGG ACA CTG GCA CAG AGC TTG ATT GAT GTC AAA GTG

AAG GAA ATC TCC AAC CAA GAG CCT TTG AAA CTC.
```

In a series of preferred embodiments, the vaccine single dose comprises $1\times10^5$ to $1\times10^7$ plaque-forming units, $1\times10^5$ to $1\times10^6$ plaque-forming units, $1\times10^5$ to $5\times10^5$ plaque-forming units or $3.4\times10^7$ plaque-forming units.

In yet another preferred embodiment, the pharmaceutically-acceptable carrier, excipient or diluent further comprises lactose and human serum albumin, most preferably at 5% (w/v) and 1% (w/v) of said formulation, respectively.

In still another preferred embodiment, the vaccine formulation further comprises neomycin of no more than 25 µg per single dose of said formulation.

In yet another preferred embodiment, the single dose is provided in a volume of 0.1 to 1.0 ml, with increments of 0.1 ml.

In still another preferred embodiment, the vaccine formulation is in a form suitable for a route of administration selected from the group consisting of subcutaneous, intramuscular and intradermal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 Amino acid sequence (SEQ ID NO: 1) of Hantaan virus G1 glycoprotein. Bracketed region ([. . .]) indicate potentially cleaved residues.

FIG. 2 Amino acid sequence (SEQ ID NO: 2) of Hantaan virus G2 glycoprotein.

FIG. 3 Amino acid sequence (SEQ ID NO: 3) of Hantaan virus nucleocapsid N protein.

FIG. 4 Nucleotide sequence (SEQ ID NO: 4) of Hantaan virus M segment cDNA.

FIG. 5. Nucleotide sequence (SEQ 10 NO: 5) of Hantaan virus S segment c DNA.

DETAILED DESCRIPTION OF THE INVENTION

Vaccinia virus is a member of the Orthopox genus of the Poxvirus family with little virulence for humans. Although the exact origin of vaccinia virus is obscure, it is related to the cowpox virus used by Jenner and strains of vaccinia virus became the vaccines of choice for the prevention of smallpox. Baxby, "Vaccinia Virus," in *VACCINIA VIRUSES AS VECTORS FOR VACCINE ANTIGENS*. G. V. Quinnan, ed., Elsevier, New York, N.Y., pp. 3–8 (1985). The smallpox vaccines used in the eradication effort were prepared on large scale by inoculating the shave abdomens of calves, sheep or water buffalo with seed stocks of vaccinia virus and harvesting the infected exudative lymph from the inoculation sites. Henderson and Arita, "Utilization of Vaccine in the Global Eradication of Smallpox," *VACCINIA VIRUSES AS VECTORS FOR VACCINE ANTIGENS*. G. V. Quinnan, ed., Elsevier, New York, N.Y., pp. 61–67 (1985). The novelty of the vaccination procedure used by Jenner caused alarm with some of his contemporaries. The ultimate eradication of smallpox following implementation of the Intensified Smallpox Eradication Program of the World Health Organization proved that skepticism to be without foundation.

Vaccinia virus has several biological properties which make it an excellent candidate for use as a live vaccine. First, it possesses a high degree of physical and genetic stability under even severe field conditions, reducing problems and expense in transport and storage. In addition, genomic stability makes the incorporation of one or more foreign genes for the antigens to be expressed more feasible than in other systems. Second, because vaccinia replicates in the cytoplasm of host cells and uses its own DNA and RNA polymerases, effects on the host cell's physiologic functions are minimized. Third, vaccinia virus has a wide host range, thus permitting use of a single vaccine in a large number of species. Fourth, both humoral and cellular immunity are mediated by vaccinia virus-based vaccines. And fifth, the duration of effectiveness of vaccinia immunization is relatively long. See Haber et al., *Science* 243: 51 (1989). Much of the early work geared towards a vaccinia virus vector was undertaken with vaccine development in mind. Weir et al., *Proc. Nat'l Acad. Sci.* USA 79: 1210–14 (1982); Mackett et al., *Proc. Nat'l Acad. Sci. USA* 79: 7415–19 (1982); Smith et al., *Nature* 302: 490–95 (1983); Smith et al., *Proc. Nat'l Acad. Sci. USA* 80: 7155–59 (1983).

As with any vaccine, safety is a major concern with the use of vaccinia virus as a immunizing agent. The adverse reaction rate of 1 in 50,000, reported during smallpox vaccinations, was tolerated only because the disease it prevented was so devastating. Baxby (1985). Generalized vaccinia among persons without underlying illnesses is characterized by a vesicular rash of varying extent that is usually self-limited. In the event of the formation of skin lesions as a result of virus replication, there is a risk of bacterial superinfection. In addition, there is also a risk of the formation of a scar at the site of skin lesions if they occur. Several attenuated smallpox vaccine strains were developed but, due to lower potency, were not adopted for general use. Recent efforts towards genetic engineering of vaccinia virus have resulted in strains with decreased virulence. These efforts targeted the viral thymidine kinase, growth factor, hemagglutinin, 13.8 kD secreted protein and ribonucleotide reductase genes. Buller et al., *Nature* 317: 813 (1985); Buller et al., *J. Virol.* 62: 866 (1988); Flexner et al., *Nature* 330: 259 (1987); Shida et al., *J. Virol.* 62: 4474 (1988); Kotwal et al., *Virology* 117: 579 (1989); Child et al., *Virology* 174: 626 (1990). There also is interest in using other members of the poxvirus family, such as avipoxviruses, as limited host range vaccine vectors. Taylor et al., *Virology* 6: 497 (1988). For instance, U.S. Pat. No. 5,266,313, hereby incorporated by reference, discloses and claims a raccoon poxvirus-based vaccine for rabies virus. Thus, discussion of vaccinia in the following examples is not intended to suggest limitation of the possible vaccine vectors.

Recombinant vaccinia viruses have been used to express genes of nonviral pathogens such as bacteria, rickettsia and protozoa and, in some cases, have protected experimental animals from infection. Fields, *Science* 252: 1662–67 (1991). In addition, vaccinia-based rabies and rinderpest vaccines have been tested. Id. The human immunodeficiency virus type 1 (HIV-1) envelope glycoprotein (env) gene has been cloned into a vaccinia vector and a phase trial was conducted with this virus. The vaccine appeared safe, and demonstrated the development of readily detectable, persistent in vivo T-cell proliferative and serum antibody responses to HIV-1 in vaccinia-naive persons. Cooney et al., *Lancet* 337: 567 (1991). A neutralizing antibody response was not seen but the expression of the env gene was low compared to levels now obtainable.

The pharmaceutical compositions of the present invention are advantageously administered in the form of injectable compositions. A typical composition for such purpose comprises a pharmaceutically acceptable carrier. For instance, the composition may contain human serum albumin in a phosphate buffer containing NaCl. Other pharmaceutically acceptable carriers include aqueous solutions, non-toxic excipients, including salts, preservatives, buffers and the like (*REMINGTON'S PHARMACEUTICAL SCIENCES*, 15th Ed., Easton ed., Mack Publishing Co., pp 1405–1412 and 1461–1487 (1975) and *THE NATIONAL FORMULARY XIV*, 14th Ed., American Pharmaceutical Association, Washington, DC (1975), both hereby incorporated by reference). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, *THE PHARMACOLOGICAL BASIS FOR THERAPEUTICS* (7th ed.).

Typically, such vaccines are prepared as injectables, either as liquid solutions or suspensions; solid forms suitable for solution in, or suspension in, liquid prior to injection may also be prepared. The preparation also may be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH-buffering agents, adjuvants or immunopotentiators which enhance the effectiveness of the vaccine.

The vaccines are conventionally administered parenterally, by injection, for example, either subcutaneously or intramuscularly. Additional formulations which are suitable for other modes of administration an include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%–95% of active ingredient, preferably 25–70%.

The term "unit dose" refers to physically discrete units suitable for use in humans, each unit containing a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are on the order of one to several hundred micrograms of active ingredient per individual. Suitable regimes for initial administration and booster shots also vary but are typified by an initial administration followed in one or two week intervals by one or more subsequent injections or other administration.

The following examples are given by way of illustration and should not be construed as limiting the scope of the invention. The examples are drawn from a Investigational New Drug Application, submitted to the U.S. Food and Drug Administration on Jun. 25, 1993, entitled "Hantaan M—S (Vaccinia virus-vectored) Recombinant Vaccine (TSI-GSD 264), FDA IND NO. 5166, hereby incorporated by reference.

EXAMPLE 1

Construction of a Vaccinia-Based Hantavirus Vaccine

VACCINE CONSTRUCTION—Sequences pertinent to the construction and production of the candidate vaccine are illustrated in FIGS. 4 and 5 (SEQ ID NOS 4 and 5).

1. Expression of HFRS antigenic subunits in vaccinia virus:
  a. Construction of transfer vector plasmids.
  BglII restriction sites were engineered near the 3'- and 5'-ends of complementary DNA (cDNA) representing the Hantaan virus M genome segment by site-directed mutagenesis. Digestion with BglII generated a restriction fragment of approximately 3.5 kB which contained the entire coding regions of the G1 and G2 envelope glycoproteins. For subcloning into the SmaI site of the vaccinia virus transfer vector pSC11, the DNA was treated with the large (Klenow) fragment of DNA polymerase I to produce blunt ends. The lac Z gene in the plasmid was deleted using the restriction enzymes PstI and XhoI.

Because animal experimentation with recombinants indicated that Hantaan virus nucleocapsid (N) protein, encoded by the S segment, conferred protection against challenge with Hantaan virus in concert with the glycoproteins, the S segment was included in construction of the recombinant vaccine candidate.

b. Preparation of vaccinia virus recombinants.

For vaccinia virus recombinations, confluent monolayers of Vero E6 cells in 25-cm$^2$ flasks were infected at a multiplicity of infection of 0.03 plaque forming units (PFU) per cell with a seed vaccinia virus diluted in liquid Eagle's Minimal Essential Medium (MEM) containing Earles' salts. EMEM; Gibco, Gaithersburg, Md. This virus seed carried the designation "Conn 3E1, Vero 1, D3 in Saline A, 7, Mar. 87, 4×10$^6$ PFU/ml." The Conn 3E1 seed was a 3X plaque-purified derivative of the licensed Connaught smallpox vaccine. (Conn-Master 17633). Before use in recombinant construction, it had been passaged once in Vero cells and harvested on day 3, titering at 4×10$^6$ PFU/ml.

After incubation at 37° C. for 4 h, the medium was removed and 2 ml of fresh EMEM was added. Prior to transfection of infected cells, 20 µg of the plasmid transfer vector was diluted to 0.5 ml in a buffer containing 150 mM NaCl, 0.7 mM Na$_2$HPO$_4$, 5 mM KCl, 20 mM HEPES (N-2-hydroxyethylpiperazine-N'-2-ethanesulfonic acid) and 6 mM dextrose, adjusted to pH 7.05. Calcium chloride (25 µl of 2.5M) was added slowly and the solution was incubated at room temperature for 0.5 to 1.0 h. The transfection mixture was added dropwise to the infected cell culture supernatants and cells were then incubated at 37° C. for 3 h, after which the medium was removed. A virus-neutralizing antibody and fresh EMEM was added. The cells were incubated at 37° C. until cytopathic effects were extensive and most of the cells had detached from the flask (4 to 5 days). Cells were then pelleted from the cell culture supernatant by centrifugation (8,000×g) and suspended in 10 mM Tris-HCl (pH 8.8). After two cycles of free-thawing (−70° C./37° C.), cells were sonicated on ice four times for 30 seconds each at a maximum output in a cup sonicator.

Because the lac Z gene had been removed from the plasmid transfer vector, recombinants could no longer be selected from wild-type vaccinia viruses by color. Consequently, an immunoplaque assay selection procedure was implemented. Confluent monolayers of Vero C1008 cells (Vero E6 cells, ATCC, CRL 1586) in 60 mm Petri dishes were infected with 10$^{-1}$ to 10$^{-3}$ dilutions of recombinant vaccinia viruses overlaid with EMEM, 5% fetal bovine serum and 50 µg/ml gentamicin. Two days after infection, or when vaccinia virus plaques were clearly visible, medium was removed and monolayers rinsed once with physiological saline.

A 57 mm dry, nitrocellulose filter (Schleicher and Schuell, Keene, NH, BA85) was placed on the top of the monolayers and a piece of Whatman 3MM filter paper soaked in TBST buffer (10 mM Tris-HCl (pH 8.0), 150 mM NaCl, 0.05% Tween 20) was placed on top of the nitrocellulose. The filter and paper were left in place for about 5 min, after which the nitrocellulose was removed and placed in a blocking solution consisting of TBST and 10% calf serum. The filters were rocked at room temperature for 1 h.

The blocking solution was then replaced with polyclonal, hyperimmune, mouse ascitic fluid or monoclonal antibody ascitic fluid to Hantaan virus proteins diluted 1:500 in TBST and 10% calf serum. Normal mouse ascitic fluid was used for control assays. The filters were again rocked for 1 hour at room temperature, after which they were washed three times for 10 minutes each with TBST. Alkaline phosphatase-conjugated rabbit anti-mouse IgG (Promega Biotec, Madison, Wis.), diluted 1:4000 in TBST was incubated with the washed filters by rocking at room temperature for 10 min with TBST followed by incubation with a color developer solution consisting of 330 µg NBT and 165 µg BCIP/ml (Promega Biotec, Madison, Wis.) dissolved in 100 mM Tris-HCl (pH 9.7) and 100 mM MgCl. Color development was stopped after 5–10 minutes by rinsing the filters with sterile distilled water.

To recover recombinant viruses, dark purple spots on the filters were cut out with sharp scissors and placed into sterile 10 mM Tris-HCl (pH 8.8). The filter pieces in buffer were either frozen at −70° C. until needed or were sonicated on ice at maximum output in a cup sonicator three times for 30 seconds and then assayed immediately. Three successive immunoselections were then performed. For all assays beyond the first selection, recombinant viruses were sonicated and then filtered through 0.45 µm filters in order to ensure that plaques resulted from infection of a single vaccinia virus. Plaques obtained from recombinants expressing both the M and S segments were detectable with monoclonal antibodies to N, G1, G2, or with anti-Hantaan virus polyclonal ascitic fluid.

Following the three immunoplaque selections, two standard plaque assays under agarose were then performed by infecting confluent monolayers of Vero E6 cells in 60 mm dishes for 1 h and overlaying the infected cells with EMEM containing 5% fetal bovine serum, 50 µg/ml gentamicin and 1% agarose (SeaKem, FMC Corp., Marine Colloids Div., Rockland, Me.). Random, visible plaques were picked with a sterile Pasteur pipette.

The recombinant viruses were then transferred to a vaccine production laboratory where additional plaque purification in certified cells was performed. Individual plaques previously recovered were diluted in EMEM, sonicated and plaque-purified three additional times from agarose-covered monolayers of a certified lot of MRC-5 human diploid lung cells (ATCC, CCL 171). Assays were performed in a decontaminated biological safety hood within the Vaccine Production Laboratory at United States Army Medical Research Institute of Infectious Disease (USAMRIID) in which no other infectious agents were being investigated. At each passage, plaque harvests were sonicated in sterile, physiologic saline and filtered through 0.45 µm filters to reduce the possibility of vaccinia aggregation. An individual plaque picked from the third assay was used to infect certified MRC-5 cells and a small virus seed stock was prepared. This thrice plaque-purified virus stock, designated "HTN-REC VAX#3, 3pp MRC-5/VERO, HTN-M+HTN-S, MAR 90," was transferred to The Salk Institute—Government Services Division (TSI-GSD) in Swiftwater, Pa. There, it was expanded to produce a master seed in certified MRC-5 cells (see below).

c. Expression of Hantaan genes.

The lot #1 candidate double-recombinant vaccine (expressing Hantaan virus glycoprotein and nucleocapsid products) was examined by radiolabeling and electrophoresis of immunoprecipitated proteins. The proteins produced were indistinguishable from the authentic Hantaan virus proteins. Comparison of previous vaccinia recombinants expressing the M and S gene demonstrated that comparable levels of Hantaan envelope proteins G1 and G2 were produced with each recombinant. Amounts of radiolabeled N protein appeared considerably greater in the new recombinant vaccine. This might be due to improved expression of the S gene under control of the vaccinia virus 11 kD promoter, as opposed to the 7.5 kD promoter used in the previous recombinant. Wittek et al., *J. Virol.* 49: 371–378 (1984).

EXAMPLE 2

Manufacture of Seed Stocks and Vaccine Lots

Methods

1. Seed Stocks:

a. Master Seed.

The thrice plaque-purified virus stock, designated "HTN-REC VAX#3, 3 pp MRC-5/VERO, HTN-M+HTN-S, MAR 90" (see above), was transferred to TSI-GSD for manufacture in certified MRC-5 cells. The production process is described briefly below. A 1:100 dilution of the seed material was used to inoculate 200 tissue culture flasks (150 cm$^2$) of MRC-5 cells for production of master seed virus. Infected cells were harvested by centrifugation. After blending and sonicating the infected cells, virus was partially purified by centrifugation in sucrose. The resultant freeze-dried master seed, designated NTOO87, was stabilized with 1 gm percent human serum albumin (HSA).

b. Production Seed.

The Master Seed (NTOO87) was used for the manufacture of a production seed according to the following protocol. Two hundred tissue culture flask (150 cm$^2$) cultures of MRC-5 cells were infected with a 1:100 dilution of the master seed virus. Infected cells were incubated to 4+ cytopathic effect (CPE). "4+ CPE" indicates total or near total loss of cell viability, characterized by loss of adherence to the growth vessel. Cells were harvested, blended and sonicated and the virus was then partially purified by sucrose centrifugation. HSA was added to 4% (v/v) as stabilizer and then this Production Seed, designated NTOO88, was freeze-dried under standard conditions. A Production Seed Control Fluid, designated NTO588, was prepared in parallel from uninfected cultures.

c. Lot 1.

Lot 1 of the recombinant vaccinia-vectored Hantaan vaccine was prepared by infecting 280 tissue culture flask (150 cm$^2$) cultures of MRC-5 cells with a 1:100 dilution of Production Seed virus (NTOO88). The cultures were incubated for 3 days at which time cytopathic effect was maximum (4+). Infected cells were harvested and later frozen, thawed, blended, sonicated, clarified and resuspended. The resuspended material was frozen again. To begin purification of the bulk, the frozen material was thawed, sonicated, and pooled before concentration to 320 ml volume using a 300,000 MW low-protein binding membrane. This concentrated bulk was sonicated and then partially purified by centrifugation through sucrose. Fractions were titered and those with an acceptable titer (2.0×10$^8$ PFU/ml) were pooled, giving a volume of 380 ml. This pool was dialyzed versus phosphate buffered saline (PBS) without calcium or magnesium (MR0039) to reduce the sucrose from 38% to 2.0% and then combined with an equal volume of stabilizer (10% lactose with 2 gm percent HSA). This material was then dispensed in 1 ml aliquots in sterile 6.5 ml vials and freeze-dried as "Lot 1-1-90" of the vaccine candidate, with the product number designation of TSI-GSD-264.

Control (uninfected) fluid was prepared at each step by shell-freezing the cells in EMEM and then blending, sonicating, centrifuging and supplementing with HSA. Routine safety testing of final bulk, final container and control fluids was satisfactory. These tests included bacterial sterility, including in vitro Mycobacterium culture, mycoplasma culture in broth and on agar, tissue culture testing for adventitious agents and general safety in mice after intracerebral inoculation.

EXAMPLE 3

Composition and Storage of Live Hantavirus (TSI-GSD 264, Lot #1-1-90 (Lot #1))

The product is a freeze-dried preparation of cell-cultured, Hantaan M+S recombinant vaccinia virus grown in certified MRC-5 cells at 35° C. in Eagle's Minimum Essential Medium (EMEM) with 5% fetal bovine serum. After purification, the fetal bovine serum was reduced to an insignificant amount. The fetal bovine serum is removed during virus concentration with the Minitan tangential flow device (Millipore). The 300,000 MW cut-off retains virus particles and flushes out fetal bovine serum components. Any residual fetal bovine serum is incapable of penetrating the 30–60% sucrose gradient through which virus was run. Virus was retrieved from the 41–49% sucrose fractions. Final purified vaccine product was stabilized to a final concentration of 5% lactose and 1 gm percent human serum albumin (HSA), freeze-dried and sealed in an atmosphere of sterile, dry nitrogen. Each vial of dried product contains approximately 6.76×10$^7$ PFU/ml. Due to variability in assaying for PFU, some variations may occur from test to test.

EXAMPLE 4

Safety Test of Hantavirus Vaccine for Adventitious Agents

Objective

To remove vaccinia virus from a preparation while other viruses remain.

Background

1. Type protocol for removal of vaccinia with 0.45 μm filter (Nalgene model 245–0045) was provided by Dr. Smith of the Food and Drug Administration (FDA). This protocol had been abstracted from a submission accepted by the FDA for a vaccinia product manufactured by an anonymous company.

2. Results reported in subject protocol could not be duplicated. It is possible that the difference is in the effect of sonication. In the original study, sonication may have failed to dissociate virus from membranes so that it was removed by filtration. In contrast, we may have successfully dissociated the virus using what is presumed to be the same procedure and, as a consequence, could only partially remove the virus by filtration.

3. Preliminary experimentation with a number of vaccinia-specific antisera of human, rabbit and lymphocyte hybridoma origin demonstrated that vaccinia virus is not efficiently neutralized. We found that monoclonal antibody 7D11 was superior to all others tested, but could not neutralize more than 10$^5$ virions. Thus, it was obvious that it would be necessary to remove any virus in excess of that amount (vaccine typically contains 10$^9$ virions) before it could be tested successfully in the tissue culture safety test.

4. These factors necessitated additional modification of the protocol. Therefore, the filtration process was repeated a second time to reduce the pre-neutralization titer to $10_5$ virions.

Materials and Methods

1. Test Articles and Reagents:

a. Vaccinia-infected MRC-5 cells were frozen at $-70°$ C. until used. The material was thawed and the cell debris pelleted by centrifugation. The supernatant fluid was discarded and the pellet resuspended to its original volume. This material most closely approximated that used in vaccine manufacture. This suspension was sonicated twice for 20 seconds.

b. A BHV-1 herpes virus sample was prepared using standard methodology.

c. Filter—0.45 μm Nalgene filter (Model #245-0045).

2. Virus Titration:

a. Vaccinia was titrated in triplicate using monolayers of Vero cells in 6-well plates. After adsorption of samples for 2 hours, cells were overlayed with media containing 0.6% agarose and incubated at 37° C. in a $CO_2$-rich environment for 48 h. A second overlay, the same as above except for addition of neutral red, was added and the cells were incubated an additional 24 h. Plaque titers were determined by standard procedures.

b. Herpes virus was titrated in triplicate using monolayers of bovine turbinate cells in 6-well plates as described above except that a single overlay was used. After 72 hours incubation, the cells were fixed with 10% buffered formalin and the agar overlay was removed. The cells were then stained by flooding with crystal violet and plaque titers determined.

Procedures and Results

The vaccinia and herpesvirus pools were titrated before filtration. The pools were then filtered through a Nalgene 0.45 μm filter (#245-0045), sampled, refiltered through a second filter and then resampled. Samples were titrated as summarized below.

TABLE 1

| Sample | Virus titer ($\log_{10}$ PFU/ml) | |
| --- | --- | --- |
| | Vaccinia | Herpes |
| Prefiltered virus pool | 8.0 | 7.56 |
| Filtered one time | 6.13 | 7.12 |
| Filtered two times | 5.19 | 6.44 |

Conclusion

Vaccinia virus could be reduced to approximately $10^5$ virions by sequential passage through two Nalgene 0.45 μm filters. The residual virus could then be neutralized with monoclonal antibody.

EXAMPLE 5

Assessment of Hantavirus-Induced Dermatotropic Reaction

Objective

To compare the dermatropic properties of Hantaan (vaccinia-vectored) seed virus with an FDA reference virus.

Background

1. Traditionally, smallpox vaccine has been administered by multiple pressure inoculations. Successful primary vaccination or a "take" induces a localized skin lesion that resolves into a permanent scar. Production of this response is dependent upon dermatropic properties. These properties are estimated in the rabbit scarification test.

2. Presently, vaccine induced scars are highly undesirable. Therefore, TSI-GSD 264 vaccinia vectored Hantaan vaccine has been produced in cell culture so that it can be administered by subcutaneous or intramuscular inoculation. Consequently, retention of dermatropic properties are not essential. Nevertheless, the seed virus has been tested to ensure that the cell culture passage has not enhanced dermatropic reactogenicity.

3. Acceptability criteria is that the vaccine seed does not cause a more severe dermatropic reaction than the FDA reference vaccine.

Materials

1. Test article—Hantaan (vaccinia-vectored), production seed, Lot 1 (NT0088).

2. Control article—FDS reference vaccinia, Lot 2.

3. Test system—New Zealand White rabbits, 2 to 3 Kg, female.

Procedure

1. Rabbits were sedated with a Ketamine/Rompun mixture.

2. Hair was clipped from four, 2×5 cm areas on each side of the rabbit and scarified by vigorous rubbing with a "comb."

3. Serial dilutions of recombinant Hantaan vaccine seed and reference vaccinia virus were prepared in two sequences: (1) $\log_{10}$ dilutions 1:10 through 1: 10,000 and (2) $\log_{10}$ dilutions 1:30 through 1:30,000.

4. Rabbit 1 was inoculated by coating the scarified skin surface with 0.2 ml of dilution sequence 1 for the recombinant Hantaan vaccine on the four areas on the left side of rabbit 1. Corresponding dilutions of sequence 1 for the reference vaccine were placed on the right side of rabbit 1.

5. Rabbit 2 was treated similarly with dilution sequence 2.

6. Two additional rabbits were inoculated at two sites with the first two dilutions of the reference virus from either dilution sequence 1 or 2. Additionally, tissue reactions caused by the scarification were monitored in two rabbits by observing two scarification sites on each rabbit that were either left uninoculated or inoculated with diluent.

Results

Comparison of skin reactions were purely subjective. It was concluded, however, that the recombinant Hantaan vaccine produced a much less severe skin reaction than the FDA reference vaccine. The skin lesions produced by the Hantaan vaccine resolved and the scab was removed while the reference vaccine lesions retained a tightly attached scab.

Summary

The Hantaan (Vaccinia-Vectored) seed virus was less reactive than the FDA reference virus in the rabbit scarification test.

EXAMPLE 6

Testing of Hantavirus Vaccine for Pathogenicity in a Murine Model

Objective

To compare the mouse lethality of Hantaan M+S (vaccinia virus-vectored) vaccine with the FDA reference vaccinia vaccine Lot 2.

Materials

1. Vaccine a. Hantaan M+S (vaccinia virus-vectored) vaccine, FB0264, Lot 1.

b. FDA reference vaccinia, Lot 2.

2. Animals —<24 h old suckling mice, CD-1 strain, Charles River, Raliegh, N.C.

Procedure

1. Comparative titration of TSI and FDA vaccines were conducted in a single test using the final bulk of the Hantaan vaccine M+S (titer $2.1 \times 10^6$ PFU/0.3 ml) and FDA reference vaccine ($5.4 \times 10^7$ PFU/0.3 ml), respectively.

2. Logarithmic dilutions of the vaccine were prepared. Two litters of 5 mice each were used for each dilution. Mice were inoculated intracerebrally with 0.03 ml of the appropriate dilutions and observed for 21 days.

3. Mouse lethality was calculated as the dose in PFU that killed 50% of mice (e.g., PFU/0.03 ml of vaccine divided by $LD_{50}$ of vaccine).

Results

TABLE 2

| | Test 1. | | |
|---|---|---|---|
| Vaccine | Dose/0.03 ml | $LD_{50}$/0.03 ml | PFU/$LD_{50}$ |
| TSI | $2.1 \times 10^6$ | $1.2 \times 10^4$ | 175.0 |
| FDA | $5.4 \times 10^7$ | $1.3 \times 10^6$ | 42.9 |

TABLE 3

| Test 2 (only data for FDA reference vaccinia shown) | | | |
|---|---|---|---|
| Vaccine | Dose/0.03 ml | $LD_{50}$/0.03 ml | PFU/$LD_{50}$ |
| FDA | $3.3 \times 10^6$ | $1.5 \times 10^6$ | 2.2 |

2. Mathematical standardization of data: The data shown above demonstrates that when the FDA reference vaccine was diluted 1:16, virulence in mice was diluted approximately proportionately. Using that observation, the mouse virulence for the FDA vaccine is calculated to be 1.4 PFU/$LD_{50}$ when given at the same titer as the M+S Hantaan virus vaccine ($2.1 \times 10^6$ PFU/0.3 ml).

Discussion

1. Mouse lethality of TSI Hantaan MS (vaccinia virus-vectored) vaccine was 175 PFU/$LD_{50}$.

2. Mouse lethality of FDA vaccinia vaccine was calculated to be 1.4 PFU/$LD_{50}$.

3. The mean time-to-death for the Hantaan was 10.76+/−4.7 days compared to 0.8+/−1.9 days for the FDA reference vaccinia.

Conclusion

The Hantaan M+S (vaccinia virus-vectored) vaccine is calculated to be 100-times less virulent than the FDA reference vaccine when administered by intracerebral inoculation to suckling mice less than 24 h old. The time-to-death also was increased markedly for the Hantaan vaccine which further indicates reduced virulence.

EXAMPLE 7

Preclinical Investigation and Characterization of Hantavirus Vaccine

The preclinical characterization of the vaccinia-vectored Hantaan vaccine, TSI-GSD-264, included comparisons with a collection of numerous vaccinia virus strains. The strains are listed in Table 4 below and the infectious virus titers noted are for virus seeds prepared by a single passage in MRC-5 cells and plaque assayed on VERO cells.

TABLE 4

| Vaccinia Virus Strains Used for Virulence Comparisons | |
|---|---|
| STRAIN | TITER (plaque forming units/ml) |
| Wyeth Strain from ATCC | $2.3 \times 10^8$ |
| Lederle Strain from ATCC | $9.5 \times 10^8$ |
| Wyeth Licensed Vaccine (Dryvax) | $2.4 \times 10^8$ |
| Eistree Strain (Lister Vaccine) from ATCC | $1.2 \times 10^8$ |
| Connaught Licensed Vaccine | $2.3 \times 10^8$ |
| IHD Strain from ATCC | $7.0 \times 10^8$ |
| Bureau of Biologics Standard Strain | $1.1 \times 10^8$ |
| Western Reserve (mouse-adapted) Strain | $6.5 \times 10^8$ |
| TSI-GSD-241 | $2.0 \times 10^8$ |
| TSI-GSD-264 | $1.2 \times 10^8$ |

TABLE 5

| Virulence Comparison of Vaccinia Virus Strains | | | |
|---|---|---|---|
| | | (minimal dose in $\log^{10}$ giving lesions) | |
| STRAINS | ADULT MOUSE VIRULENCE | DOSE ERYTHEMA | DOSE EROSION |
| Wyeth ATCC | + | 2 | 6 |
| Lederle | + | 2 | 5 |
| Wyeth Vaccine | + | 2 | 7 |
| Lister | + | 2 | 6 |
| Connaught | + | 3 | 6 |
| IHD | ++++ | 1 | 2 |
| BOB Standard | + | 2 | 5 |
| WR | ++++ | 1 | 1 |
| TSI-GSD-241 | − | 3 | 7 |
| TSI-GSD-264 | − | 4 | 7 |

Relative rating with ++++ most virulent and − avirulent.

The virus strains were examined for pock formation on chorioallantoic membranes of embryonated chicken eggs, formation of lesions after intradermal inoculation of adult rabbits, and intracerebral and intraperitoneal virulence for adult and suckling outbred mice. Representative data are presented in Table 5 above. For purposes of comparison, data are illustrated for both the vaccinia-vectored Hantaan vaccine candidate (TSI-GSD-264) and a cell-cultured smallpox vaccine (TSI-GSD-241, reference IND #4984) derived from the same virus seed ("Conn 3E1"), which in turn was a thrice plaque-picked derivation from the licensed Connaught vaccinia (Conn-Master 17633). Using these tests, both the vaccinia-vectored Hantaan vaccine candidate (TSI-GSD-264) and a cell cultured smallpox vaccine (TSI-GSD-241) were among the least virulent vaccinia strains tested and were comparable to the New York Board of Health, Bureau of Biologics reference strain.

A primary study compared the undiluted vaccinia-vectored Hantaan vaccine, TSI-GSD-264, to the licensed Wyeth vaccine, as well as to a cell-cultured smallpox vaccine (TSI-GSD-241, reference IND #4984). The TSI-GSD-264 booster was given to 4 monkeys in the study. An additional six monkeys received TSI-GSD 264 one year after immunization with vaccinia virus lacking any foreign gene insert either the cell-cultured parent virus or Wyeth Dryvax™. Intradermal and subcutaneous administration of the vaccine candidate was well tolerated and all monkeys seroconverted. Cutaneous lesions were minimal and comparable among the three vaccines tested.

Of the four monkeys receiving primary immunization with TSI-GSD 264, neutralizing antibody to Hantaan virus was detected at 42 days post-inoculation in three monkeys. The fourth monkey developed neutralizing antibody after a boost. All monkeys had seroconverted, as measured by ELISA, after primary immunization. Of the monkeys initially immunized with a non-recombinant vaccinia and later immunized with TSI-GSD 264, none developed neutralizing antibody and two developed low ELISA titers to Hantaan.

One monkey from the study died 6½ months after receiving the vaccine candidate as a primary immunization. It had not had any unusual response to immunization and its death was determined to be the result of gastric perforation. No pathologic lesions suggestive of vaccinia were noted. Another monkey which was inoculated with TSI-GSD 264 as its booster, was euthanized 8 months later because of chronic diarrhea and a generalized wasting condition attributed to Simian Retrovirus infection (SRV). Blood specimens obtained from the monkey four days prior to euthanasia were both seropositive and culture positive for SRV. In light of the fact that (i) most severe reactions to vaccinia virus inoculation occur within 30 days and (ii) these monkeys had no lesions suggestive of vaccinia virus infection, it is unlikely that these deaths were caused by inoculation with the candidate vaccine. The pathology reports are filed with the IND.

EXAMPLE 8

Human Clinical Studies with Hantavirus Vaccine

General Study Design

The preliminary phase of the study is an open label inoculation of four individuals with documented vaccinia immunization (Group 1), succeeded by inoculation of four vaccinia-naive individuals (Group 2) 21 days after the first group is inoculated. Previous vaccinia immunization are documented by medical records and unequivocal vaccinia scar. This is followed by a randomized trial in 24 vaccinia-naive volunteers (Group 3). Vaccinia immune globulin is available on site for the treatment of serious adverse reactions such as ocular, generalized or progressive vaccinia.

Group 1 (smallpox-immune) volunteers are admitted as inpatients in groups of two to four people and receive the vaccinia-vectored Hantaan vaccine candidate (open label) by the subcutaneous route. Groups 2, 3 and 4 (vaccine-naive) subjects are administered the vaccine candidate, in escalating doses, in like fashion. Inoculation is given in the deltoid region of the arm. The four vaccinia-immune individuals in Group 1 receive the vaccine in the arm in which there is no vaccinia scar from previous immunization. Previous vaccinia immunization is documented by medical records and unequivocal vaccinia scar.

Group 1, 2, 3 and 4 subjects are admitted 3 days prior to inoculation and remain as inpatients until 4 days after inoculation. Subjects are then discharged and assessed on an outpatient basis without periodic bleeding with clinical examinations for potential reactions or complications through day 21. Subjects developing a vesicular or open lesion suspected to contain vaccinia virus have the lesion covered with a dressing and are followed with subsequent daily clinical examinations and dressing changes by an investigator or the nursing staff until the lesion forms a scab.

Group 5 volunteers, all vaccinia-naive, are enrolled depending on availability as outpatient subjects. Group 5 volunteers are randomly assigned to one of two subgroups: one receives a single injection and the other receives a booster. The vaccinees are grouped as follows:

TABLE 6

| Group # | # of volunteers | vaccinia immunity | dose | booster |
|---|---|---|---|---|
| 1 (inpatient) | 4 | immune | $3.4 \times 10^5$ PFU | no |
| 2 (inpatient) | 4 | non-immune | $3.4 \times 10^5$ PFU | no |
| 3 (inpatient) | 4 | non-immune | $3.4 \times 10^6$ PFU | no |
| 4 (inpatient) | 4 | non-immune | $3.4 \times 10^7$ PFU | no |
| 5 (outpatient) | 24 randomized: | | | |
| A | | non-immune | $3.4 \times 10^7$ PFU | no |
| B | | non-immune | $3.4 \times 10^7$ PFU | yes |

On day 0, Groups 3A and 3B receive the vaccine candidate subcutaneously. After a 30 minute observation period for immediate untoward reactions, subjects are followed on an outpatient basis. Subjects have clear instructions on what to do if they experience an adverse reaction. On day 42, Group 3B receives a second injection of the vaccine. Outpatient follow-up, periodic bleeding and further clinical examinations as provided as needed.

1. Selection of Vaccine Dose:

a. The cell-cultured vaccinia virus candidate vaccine has a titer of $6.8 \times 10^7$ PFU/ml. A dose of 0.5 ml of undiluted vaccine is administered subcutaneously, equaling an inoculum of 3.4×107 PFU. Preclinical studies in animals support the immunogenicity and safety of this undiluted vaccine dose. McClain et al., American Soc. Tropical Med. Hygiene Annual Meeting (1993).

2. Clinical Procedures:

a. General Considerations.

All times mentioned below are referenced against the day of inoculation, which is customarily designated as Day 0. Physical activity one week prior to and during the first 4 weeks following inoculation is limited to each subject's usual level of activity. This minimizes abnormalities in serum enzyme levels associated with strenuous activity.

b. Inoculation and Immediate Observation.

Subjects remain under the direct supervision of the Principal Investigator or Associate Clinical Investigator for 30 minutes after inoculation. Injectable epinephrine and resuscitative equipment are available for the treatment of acute anaphylactic reaction. An aliquot of the remaining vaccine virus is retained for determination of virus titer and the remainder of the vaccine is destroyed by incineration in accordance with state regulations for disposal of medical waste.

c. Continued Inpatient Observation.

Members of Groups 1 and 2 are monitored for four days after inoculation on the inpatient ward. Temperature, pulse, respiratory rate, and blood pressure are monitored three times a day for three days prior to, and four days after, inoculation on the clinical ward. The interval between measurements is shortened in subjects with symptoms or fever (oral temperature >100.5° F.). Inoculation sites are daily examined by measurement of erythema and induration, measuring 2 perpendicular directions across the lesion. Photographs are taken as needed. Any vesicular eruption or crusting is noted and cultured for virus. During the inpatient phase, responses to inquiries about local or systemic complaints (pruritus, pain, malaise, fatigue, etc.) are recorded daily. Attempts are made to quantify the duration and severity of complaints. A scale of 0 to 3 is used to measure the degree to which symptoms interfere with activities of daily living. Evaluations are detailed on clinical evaluation forms.

d. Outpatient Observations.

Volunteers are followed with vital signs and physical examinations for up to 11 days following inoculation during the outpatient phase of the protocol. Each participant is advised that staff are available on a 24-hour basis for the duration of the study in order to screen any subject who is suffering any side effect of the inoculation. These side effects include fever, itching, rash or any other symptoms, regardless of their opinion as to the relevance of the symptom to the inoculation. The nursing staff evaluates the complaint and notes the complaint in the clinical protocol record. The nursing staff then reports all such complaints to the Principal Investigator or Associate Clinical Investigator for evaluation and instructions about required follow-up care. Any subject developing a vesicular lesion at the site of inoculation has the lesion covered with a dressing until such a lesion has formed a scab. In addition, subjects return for scheduled bleeding as per the appropriate bleed schedule. At 63 days after inoculation a clinical summary of protocol participation is entered into the clinical record for each volunteer. A copy of this summary is sent to the volunteer's official medical record unless a volunteer specifically indicates that he/she does not want this done.

3. Laboratory Studies:

a. Baseline screening laboratory studies are as described above. Protocol participation studies include periodic examinations of the following: CBC with differential and platelets, urinalysis, serum chemistries, serum viremia, serum vaccinia antibody, serum Hantaan antibody and lymphocyte immune responses to Hantaan antigen. Remaining serum samples are maintained frozen at −40° C. in the USAMRIID serum bank and available for additional studies and/or repeat of selected studies as needed, unless volunteers specifically exclude use of samples for additional studies. Fluid in vesicular or weeping lesions at the site of inoculation or at distant sites is be sampled and placed in viral isolation transport medium to attempt virus recovery. Serum antibody determinations include ELISA reactivity with whole virus Hantaan antigen and vaccinia antigen and plaque reduction neutralization of Hantaan virus.

EXAMPLE 9

Results of Clinical Trials With M+S Hantavirus (Vaccinia-Vectored) Vaccine

Clinical trials of the vaccinia-vectored M+S Hantavirus vaccine are expected to show the vaccine to be safe and effective in humans. Vaccine recipients are expected to produce significant humoral response as measured by enzyme-linked immunosorbent assays (ELISA). This response should be characterized by the production of both neutralizing and non-neutralizing antibodies, the latter being measured by plaque reduction neutralization assays. In addition, lymphocyte blastogenesis assays are expected to demonstrate that lymphoytes from vaccine recipients proliferate and produce cytokines upon exposure to Hantavirus antigen in vitro.

We claim:

1. A vaccine formulation suitable for use in a human, comprising:
   (i) infectious vaccinia virus that comprises a DNA molecule encoding
      (a) the Hantaan virus polypeptides designated N, G1 and G2, and
      (b) all vaccinia virus polypeptides necessary for replication of said virus in a cell derived from said human, but not a functional thymidine kinase; and
   (ii) a pharmaceutically-acceptable carrier, excipient or diluent,
   wherein said vaccine formulation comprises a single dose of $5 \times 10^5$ to $7 \times 10^7$ plaque forming units of vaccinia virus.

2. The vaccine formulation according to claim 1, wherein the nucleotide sequence encoding said G1 polypeptide and said G2 polypeptide is operably linked to the vaccinia virus 7.5 kD promoter, and wherein the nucleotide sequence encoding said N polypeptide is operably linked to the vaccinia virus 11 kD promoter.

3. The vaccine formulation according to claim 1, wherein said G1 has the sequence (SEQ ID NO: 1):

MET GLY ILE TRP LYS TRP LEU VAL MET ALA SER LEU VAL TRP PRO VAL LEU THR LEU ARG ASN VAL TYR

ASP MET LYS ILE GLU CYS PRO HIS THR VAL SER PHE GLY GLU ASN SER VAL ILE GLY TYR VAL GLU LEU

PRO PRO VAL PRO LEU ALA ASP THR ALA GLN MET VAL PRO GLU SER SER CYS ASN MET ASP ASN HIS GLN

SER LEU ASN THR ILE THR LYS TYR THR GLN VAL SER TRP ARG GLY LYS ALA ASP GLN SER GLN SER SER

GLN ASN SER PHE GLU THR VAL SER THR GLU VAL ASP LEU LYS GLY THR CYS VAL LEU LYS HIS LYS MET

VAL GLU GLU SER TYR ARG SER ARG LYS SER VAL THR CYS TYR ASP LEU SER CYS ASN SER THR TYR CYS

LYS PRO THR LEU TYR MET ILE VAL PRO ILE HIS ALA CYS ASN MET LYS SER CYS LEU ILE ALA LEU GLY

PRO TYR ARG VAL GLN VAL VAL TYR GLU ARG SER TYR CYS MET THR GLY VAL LEU ILE GLU GLY LYS CYS

PHE VAL PRO ASP GLN SER VAL VAL SER ILE ILE LYS HIS GLY ILE PHE ASP ILE ALA SER VAL HIS ILE VAL

CYS PHE PHE VAL ALA VAL LYS GLY ASN THR TYR LYS ILE PHE GLU GLN VAL LYS LYS SER PHE GLU SER

THR CYS ASN ASP THR GLU ASN LYS VAL GLN GLY TYR TYR ILE CYS ILE VAL GLY ASN SER ALA PRO ILE

TYR VAL PRO THR LEU ASP ASP PHE ARG SER MET GLU ALA PHE THR GLY ILE PHE ARG SER PRO HIS GLY

GLU ASP HIS ASP LEU ALA GLY GLU GLU ILE ALA SER TYR SER ILE VAL GLY PRO ALA ASN ALA LYS VAL

PRO HIS SER ALA SER SER ASP THR LEU SER LEU ILE ALA TYR SER GLY ILE PRO SER TYR SER SER LEU SER

ILE LEU THR SER SER THR GLU ALA LYS HIS VAL PHE SER PRO GLY LEU PHE PRO LYS LEU ASN HIS THR ASN

CYS ASP LYS SER ALA ILE PRO LEU ILE TRP THR GLY MET ILE ASP LEU PRO GLY TYR TYR GLU ALA VAL HIS

PRO CYS THR VAL PHE CYS VAL LEU SER GLY PRO GLY ALA SER CYS GLU ALA PHE SER GLU GLY GLY ILE

PHE ASN ILE THR SER PRO MET CYS LEU VAL SER LYS GLN ASN ARG PHE ARG LEU THR GLU GLN GLN VAL

ASN PHE VAL CYS GLN ARG VAL ASP MET ASP ILE VAL VAL TYR CYS ASN GLY GLN ARG LYS VAL ILE LEU

THR LYS THR LEU VAL ILE GLY GLN CYS ILE TYR THR ILE THR SER LEU PHE SER LEU LEU PRO GLY VAL

ALA HIS SER ILE ALA VAL GLU LEU CYS VAL PRO GLY PHE HIS GLY TRP ALA THR ALA ALA LEU LEU VAL

THR PHE CYS PHE GLY TRP VAL LEU ILE PRO ALA ILE THR PHE ILE ILE LEU THR VAL LEU LYS PHE ILE ALA

ASN ILE PHE HIS THR SER ASN GLN GLU ASN ARG LEU LYS SER VAL LEU ARG LYS ILE LYS GLU GLU PHE

GLU LYS THR LYS GLY SER MET VAL CYS ASP VAL CYS LYS TYR GLU CYS GLU THR TYR LYS GLU LEU LYS

ALA HIS GLY VAL SER CYS PRO GLN SER GLN CYS PRO TYR CYS PHE THR HIS CYS GLU PRO THR GLU ALA

ALA PHE GLN ALA HIS TYR LYS VAL CYS GLN VAL THR HIS ARG PHE ARG ASP ASP LEU LYS LYS THR VAL

THR PRO GLN ASN PHE THR PRO GLY CYS TYR ARG THR LEU ASN LEU PHE ARG TYR LYS SER ARG CYS TYR

ILE PHE THR MET TRP ILE PHE LEU LEU VAL LEU GLU SER ILE LEU TRP ALA ALA SER ALA, said G2 has the sequence (SEQ ID NO: 2):

SER GLU THR PRO LEU THR PRO VAL TRP ASN ASP ASN ALA HIS GLY VAL GLY SER VAL PRO MET HIS THR

ASP LEU GLU LEU ASP PHE SER LEU THR SER SER SER LYS TYR THR TYR ARG ARG LYS LEU THR ASN PRO

LEU GLU GLU ALA GLN SER ILE ASP LEU HIS ILE GLU ILE GLU GLN THR ILE GLY VAL ASP VAL HIS ALA

LEU GLY HIS TRP PHE ASP GLY ARG LEU ASN LEU LYS THR SER PHE HIS CYS TYR GLY ALA CYS THR LYS

TYR GLU TYR PRO TRP HIS THR ALA LYS CYS HIS TYR GLU ARG ASP TYR GLN TYR GLU THR SER TRP GLY

CYS ASN PRO SER ASP CYS PRO GLY VAL GLY THR GLY CYS THR ALA CYS GLY LEU TRY LEU ASP GLN LEU

LYS PRO VAL GLY SER ALA TYR LYS ILE ILE THR ILE ARG TYR SER ARG ARG VAL CYS VAL GLN PHE GLY GLU GLU ASN LEU CYS LYS ILE ILE ASP MET ASN ASP CYS PHE VAL SER ARG HIS VAL LYS VAL CYS ILE ILE GLY THR VAL SER LYS PHE SER GLN GLY ASP THR LEU LEU PHE PHE GLY PRO LEU GLU GLY GLY GLY LEU ILE PHE LYS HIS TRP CYS THR SER THR CYS GLN PHE GLY ASP PRO GLY ASP ILE MET SER PRO ARG ASP LYS GLY PHE LEU CYS PRO GLU PHE PRO GLY SER PHE ARG LYS LYS CYS ASN PHE ALA THR THR PRO ILE CYS GLU TYR ASP GLY ASN MET VAL SER GLY TYR LYS LYS VAL MET ALA THR ILE ASP SER PHE GLN SER PHE ASN THR SER THR MET HIS PHE THR ASP GLU ARG ILE GLU TRP LYS ASP PRO ASP GLY MET LEU ARG ASP HIS ILE ASN ILE LEU VAL THR LYS ASP ILE ASP PHE ASP ASN LEU GLY GLU ASN PRO CYS LYS ILE GLY LEU GLN THR SER SER ILE GLU GLY ALA TRP GLY SER GLY VAL GLY PHE THR LEU THR CYS LEU VAL SER LEU THR GLU CYS PRO THR PHE LEU THR SER ILE LYS ALA CYS ASP LYS ALA ILE CYS TYR GLY ALA GLU SER VAL THR LEU THR ARG GLY GLN ASN THR VAL LYS VAL SER GLY LYS GLY GLY HIS SER GLY SER THR PHE ARG CYS CYS HIS GLY GLU ASP CYS SER GLN ILE GLY LEU HIS ALA ALA ALA PRO HIS LEU ASP LYS VAL ASN GLY ILE SER GLU ILE GLU ASN SER LYS VAL TYR ASP ASP GLY ALA PRO GLN CYS GLY ILE LYS CYS TRP PHE VAL LYS SER GLY GLU TRP ILE SER GLY ILE PHE SER GLY ASN TRP ILE VAL LEU ILE VAL LEU CYS VAL PHE LEU LEU PHE SER LEU VAL LEU LEU SER ILE LEU CYS PRO VAL ARG LYS HIS LYS LYS SER and said N has the sequence (SEQ ID NO: 3):

MET ALA THR MET GLU GLU LEU GLN ARG GLU ILE ASN ALA HIS GLU GLY GLN LEU VAL ILE ALA ARG GLN LYS VAL ARG ASP ALA GLU LYS GLN TYR GLU LYS ASP PRO ASP GLU LEU ASN LYS ARG THR LEU THR ASP ARG GLU GLY VAL ALA VAL SER ILE GLN ALA LYS ILE ASP GLU LEU LYS ARG GLN LEU ALA ASP ARG ILE ALA THR GLY LYS ASN LEU GLY LYS GLU GLN ASP PRO THR GLY VAL GLU PRO GLY ASP HIS LEU LYS GLU ARG SER MET LEU SER TYR GLY ASN VAL LEU ASP LEU ASN HIS LEU ASP ILE ASP GLU PRO THR GLY GLN THR ALA ASP TRP LEU SER ILE ILE VAL TYR LEU THR SER PHE VAL VAL PRO ILE LEU LEU LYS ALA LEU TYR MET LEU THR THR ARG GLY ARG GLN THR THR LYS ASP ASN LYS GLY THR ARG ILE ARG PHE LYS ASP ASP SER SER PHE GLU ASP VAL ASN GLY ILE ARG LYS PRO LYS HIS LEU TYR VAL SER LEU PRO ASN ALA GLN SER SER MET LYS ALA GLU GLU ILE THR PRO GLY ARG TYR ARG THR ALA VAL CYS GLY LEU TYR PRO ALA GLN ILE LYS ALA ARG GLN MET ILE SER PRO VAL MET SER VAL ILE GLY PHE LEU ALA LEU ALA LYS ASP TRP SER ASP ARG ILE GLU GLN TRP LEU ILE GLU PRO CYS LYS LEU LEU PRO ASP THR ALA ALA VAL SER LEU LEU GLY GLY PRO ALA THR ASN ARG ASP TYR LEU ARG GLN ARG GLN VAL ALA LEU GLY ASN MET GLU THR LYS GLU SER LYS ALA ILE ARG GLN HIS ALA GLU ALA ALA GLY CYS SER MET ILE GLU ASP ILE GLU SER PRO SER SER ILE TRP VAL PHE ALA GLY ALA PRO ASP ARG CYS PRO PRO THR CYS LEU PHE ILE ALA GLY ILE ALA GLU LEU GLY ALA PHE PHE SER ILE LEU GLN ASP MET ARG ASN THR ILE MET ALA SER LYS THR

VAL GLY THR SER GLU GLU LYS LEU ARG LYS LYS SER SER PHE TYR GLN SER TYR LEU ARG ARG THR GLN SER MET GLY ILE GLN LEU GLY GLN ARG ILE ILE VAL LEU PHE MET VAL ALA TRP GLY LYS GLU ALA VAL ASP ASN PHE HIS LEU GLY ASP ASP MET ASP PRO GLU LEU ARG THR LEU ALA GLN SER LEU ILE ASP VAL LYS VAL LYS GLU ILE SER ASN GLN GLU PRO LEU LYS LEU.

4. The vaccine formulation according to claim 3, wherein said DNA molecule comprises a wild-type vaccinia virus genome with the cDNA of the M and S genomic segments of the Hantaan serotype inserted in the vaccinia virus thymidine kinase coding region.

5. The vaccine formulation according to claim 4, wherein said cDNA comprises the sequence (SEQ ID NO: 4):

ATG GGG ATA TGG AAG TGG CTA GTG ATG GCC AGT TTA GTA TGG CCT GTT TTG ACA CTG AGA AAT GTC

TAT GAC ATG AAA ATT GAG TGC CCC CAT ACA GTA AGT TTT GGG GAA AAC AGT GTG ATA GGT TAT GTA

GAA TTA CCC CCC GTG CCA TTG GCC GAC ACA GCA CAG ATG GTG CCT GAG AGT TCT TGT AAC ATG GAT

AAT CAC CAA TCG TTG AAT ACA ATA ACA AAA TAT ACC CAA GTA AGT TGG AGA GGA AAG GCT GAT CAG

TCA CAG TCT AGT CAA AAT TCA TTT GAG AGA GTG TCC ACT GAA GTT GAC TTG AAA GGA ACA TGT GTT

CTA AAA CAC AAA ATG GTG GAA GAA TCA TAC CGT AGT AGG AAA TCA GTA ACC TGT TAC GAC CTG TCT

TGC AAT AGC ACT TAC TGC AAG CCA ACA CTA TAC ATG ATT GTA CCA ATT CAT GCA TGC AAT ATG ATG

AAA AGC TGT TTG ATT GCA TTG GGA CCA TAC AGR GTA CAG GTG GTT TAT GAG AGA AGT TAC TGT ATG

ACA GGA GTC CTG ATT GAA GGG AAA TGC TTT GTC CCA GAT CAA AGT GTG GTC AGT ATT ATC AAG CAT

GGG ATC TTT GAT ATT GCA AGT TTT CAT ATT GTA TGT TTC TTT GTT GCA GTT AAA GGG AAT ACT TAT AAA

ATT TTT GAA CAG GTT AAG AAA TCC TTT GAA TCA ACA TGC AAT GAT ACA GAG AAT AAA GTG CAA GGA

TAT TAT ATT TGT ATT GTA GGG GGA AAC TCT GCA CCA ATA TAT GTT CCA ACA CTT GAT GAT TTC AGA

TCC ATG GAA GCA TTT ACA GGA ATC TTC AGA TCA CCA CAT GGG GAA GAT CAT GAT CTG GCT GGA GAA

GAA ATT GCA TCT TAT TCT ATA GTC GGA CCT GCC AAT GCA AAA GTT CCT CAT AGT GCT AGC TCA GAT

ACA TTG AGC TTG ATT GCC TAT TCA GGT ATA CCA TCT TAT TCT TCC CTT AGC ATC CTA ACA AGT TCA ACA

GAA GCT AAG CAT GTA TTC AGC CCT GGG TTG TTC CCA AAA CTT AAT CAC ACA AAT TGT GAT AAA AGT

GCC ATA CCA CTC ATA TGG ACT GGG ATG ATT GAT TTA CCT GGA TAC TAC GAA GCT GTC CAC CCT TGT

ACA GTT TTT GCC GTA TTA TCA GGT CCT GGG GCA TCA TGT GAA GCC TTT TCT GAA GGC GGG ATT TTC

AAC ATA ACC TCT CCC ATG TGC TTA GTG TCA AAA CAA AAT CGA TTC CGG TTA ACA GAA CAG CAA GTG

AAT TTT GTG TGT CAG CGA GTG GAC ATG GAC ATT GTT GTG TAC TGA AAC GGG CAG AGG AAA GTA ATA

TTA ACA AAA ACT CTA GTT ATT GGA CAG TGT ATA TAT ACT ATA ACA AGC TTA XXX TCA TTA CTA CCT

GGA GTA GCA CAT TCT ATT GCT GTT GAA TTG TGT GTA CCT GGG TTC ATT GGT TGG GCC ACA GCT GCT

CTG CTT GTT ACA TTC TGT TTC GGA TGG GTT CTT ATA CCA GCA ATT ACA TTT ATC ATA CTA ACA GTC CTA

AAG TTC ATT GCT AAT AAT TTT CAC ACA AGT AAT CAA GAG AAT AGG CTA AAA TCA GTA CTT AGA AAG

ATA AAG GAA GAG TTT GAA AAA ACA AAA GGC TCA ATG GTA TGT GAT GTC TGC AAG TAT GAG TGT GAA

ACA TAT AAA GAA TTA AAG GCA CAC GGG GTA TCA TGC CCC CAA TCT CAA TGT CCT TAC TGT TTT ACT

CAT TGT GAA CCT ACA GAA GCA GCA TTC CCA GTC CAT TAC AAG GTA TGC CAA GTT ACT CAC AGA TTC

AGG GAT GAT CTA AAG AAA ACT GTT ACT CCT CAA AAT TTT ACA CCA GGA TGT TAC CGG ACA CTA AAT

TTA TTT AGA TAC AAA AGC AGG TGC TAC ATC TTT ACA ATG TGG ATA TTT CTT CTT GTC TTA GAA TCC ATA

CTG TGG GCT GCA AGT GCA TCA GAG ACA CCA TTA ACT CCT GTC TGG AAT GAC AAT GCC CAT GGG GTA

GGT TCT GTT CCT ATG CAT ACA GAT TTA GAG CTT GAT TTC TCT TTA ACA TCC AGT TCC AAG TAT ACA TAC

-continued

CGT AGG AAG TTA ACA AAC CCA CTT GAG GAA GCA CAA TCC ATT GAC CTA CAT ATT GAA ATA GAA GAA
CAG ACA ATT GGT GTT GAT GTG CAT GCT CTA GGA CAC TGG TTT GAT GGT CGT CTT AAC CTT AAA ACA
TCC TTT CAC TGT TAT GGT GCT TGT ACA AAG TAT GAA TAC CCT TGG CAT ACT GCA AAG TGC CAT TAT
GAA AGA GAT TAC CAA TAT GAA ACG AGC TGG GGT TGT AAT CCA TCA GAT TGT CCT GGG GTG GGC ACA
GGC TGT ACA GCA TGT GGT TTA TAC CTA GAT CAA CTG AAA CCA GTT GGT AGT GCT TAT AAA ATT ATC
ACA ATA AGG TAC AGC AGG AGA GTC TGT GTT CAG TTT GGG GAG GAA AAC CTT TGT AAG ATA ATA GAG
ATG AAT GAT TGT TTT GTA TCT AGG CAT GTT AAG GTC TGC ATA ATT GGT ACA GTA TCT AAA TTC TCT CAG
GGT GAT ACC TTA TTG TTT TTT GGA CCG CTT GAA GGT GGT GGT CTA ATA TTT AAA CAC TGG TGT ACA
TCC ACA TGT CAA TTT GGT GAC CCA GGA GAT ATC ATG AGT CCA AGA GAC AAA GGT TTT TTA TGC CCT
GAG TTT CCA GGT AGT TTC AGG AAG AAA TGC AAC TTT GCT ACT ACC CCT ATT TGT GAG TAT GAT GGA
AAT ATG GTC TCA GGT TAC AAG AAA GTG ATG GCG ACA ATT GAT TCC TTC CAA TCT TTT AAT ACA AGC
ACT ATG CAC TTC ACT GAT GAA AGG ATA GAG TGG AAA GAC CCT GAT GGA ATG CTA AGG GAC CAT ATA
AAC ATT TTA GTA ACG AAG GAC ATT GAC TTT GAT AAC CTT GGT GAA AAT CCT TGC AAA ATT GGC CTA
CAA ACA TCT TCT ATT GAG GGG GCC TGG GGT TCT GGT GTG GGG TTC ACA TTA ACA TGT CTG GTA TCA
CTA ACA GAA TGT CCT ACC TTT TTG ACC TCA ATA AAG GCT TGT GAT AAG GCT ATC TGT TAT GGT GCA
GAG AGT GTA ACA TTG ACA AGA GGA CAA AAT ACA GTC AAG GTA TCA GGG AAA GGT GGC CAT AGT GGT
TCA ACA TTT AGG TGT TGC CAT GGG GAG GAC TGT TCA CAA ATT GGA CTC CAT GCT GCT GCA CCT CAC
CTT GAC AAG GTA AAT GGG ATT TCT GAG ATA GAA AAT AGT AAA GTA TAT GAT GAT GGG GCA CCG CAA
TGT GGG ATA AAA TGT TGG TTT GTT AAA TCA GGG AAT GGA TT TCA GGG ATA TTC AGT GGT AAT TGG
ATT GTA CTC ATT GTC CTC TGT GTA TTT CTA TTG TTC TCC TTG GTT TTA CTA AGC ATT CTC TGT CCC GTA
AGG AAG CAT AAA AAA TCA and (SEQ ID NO: 5):

ATG GCA ACT ATG GAG GAA TTA CAG AGG GAA ATC AAT GCC CAT GAG GGT CAA TTA GTG ATA GCC AGG
CAG AAG GTG AGG GAT GCA GAA AAA CAG TAT GAA AAG GAT CCA GAT GAG TTG AAC AAG AGA ACA TTA
ACT GAC CGA GAG GGC GTT GCA GTA TCT ATC CAG GCA AAA ATT GAT GAG TTA AAA AGG CAA CTG GCA
GAT AGG ATT GCA ACT GGG AAA AAC CTT GGG AAG GAA CAA GAT CCA ACA GGG GTG GAG CCT GGA GAC
CAT CTG AAA GAG AGG TCA ATG CTC AGT TAT GGT AAT GTG CTG GAT TTA AAC CAT TTG GAT ATT GAT
GAA CCT ACA GGA CAG ACA GCA GAC TGG CTG AGC ATC ATC GTC TAT CTT ACA TCC TTT GTC GTC CCG
ATA CTT CTG AAA GTC CTG TAT ATG TTG ACA ACA AGG GGG AGG CAA ACT ACC AAG GAT AAT AAA GGG
ACC CGG ATT CGA TTT AAG GAT GAT AGC TCG TTC GAG GAT GTT AAC GGT ATC CGG AAA CCA AAA CAT
CTT TAC GTG TCC TTG CCA AAT GCA CAG TCA AGC ATG AAG GCA GAA GAG ATT ACA CCT GGT AGA TAT
AGA ACA GCA GTC TGT GGG CTC TAC CCT GCA CAG ATT AAG GCA CGG CAG ATG ATC AGT CCA GTT ATG
AGT GTA ATT GGT TTT CTA GCA TTA GCA AAG GAC TGG AGT GAT CGT ATC GAA CAA TGG TTA ATT GAA
CCT TGC AAG CTT CTT CCA GAT ACA GCA GCA GTT AGC CTC CTC GGT GGT CCT GCA ACA AAC AGG GAC
TAC TTA CGG CAG CGG CAA GTG GCA TTA GGC AAT ATG GAG ACA AAG GAG TCA AAG GCT ATA CGC AGG
CAT GCA GAA GCA GCT GGC TGT AGC ATG ATT GAA GAT ATT GAG TCA CCA TCA TCA ATA TGG GTT TTT
GCT GGA GCA CCA GAC CGT TGT CCA CCA ACA TGT TTG TTT ATA GCA GGT ATT GCT GAG CTT GGG GCA
TTT TTT TCC ATC CTG CAG GAC ATG CGA AAT ACA ATC ATG GCA TCT AAG ACR GTT GGA ACA TCT GAG
GAG AAG CTA CGG AAG AAA TCA TCA TTT TAT CAG TCC TAC CTC AGA AGG ACA CAA TCA ATG GGG ATA

-continued

CAA CTA GGC CAG AGA ATT ATT GTG CTC TTC ATG GTT GCC TGG GGA AAG GAG GCT GTG GAC AAC TTC

CAC TTA GGG GAT GAT ATG GAT CCT GAG CTA AGG ACA CTG GCA CAG AGC TTG ATT GAT GTC AAA GTG

AAG GAA ATC TCC AAC CAA GAG CCT TTG AAA CTC.

6. The vaccine formulation according to claim 1, wherein said single dose comprises $5 \times 10^5$ to $7 \times 10^7$ plaque-forming units.

7. The vaccine formulation according to claim 1, wherein said single dose comprises $5 \times 10^5$ to $1 \times 10^6$ plaque-forming units.

8. The vaccine formulation according to claim 1, wherein said single dose comprises $5 \times 10^5$ to plaque-forming units.

9. The vaccine formulation according to claim 1, wherein said single dose comprises $3.4 \times 10^7$ plaque-forming units.

10. The vaccine formulation according to claim 9, wherein said pharmaceutically-acceptable carrier, excipient or diluent further comprises lactose and human serum albumin.

11. The vaccine formulation according to claim 10, wherein said lactose is 5% (w/v) of said formulation and said human serum albumin is 1% (w/v) of said formulation.

12. The vaccine formulation according to claim 11, wherein said formulation further comprises neomycin of no more than 25 µg per single dose of said formulation.

13. The vaccine formulation according to claim 12, wherein said single dose of said formulation is in a volume of 0.1 to 1.0 ml.

14. The vaccine formulation according to claim 1, wherein said formulation is in a form suitable for a route of administration selected from the group consisting of subcutaneous, intramuscular and intradermal.

15. A method for inducing a Hantavirus-protective immune response in a human, comprising the steps of:
  (i) providing a vaccine formulation suitable for use in a human comprising
    (a) infectious vaccinia virus activity and comprising a DNA molecule encoding
      (1) the Hantaan virus polypeptides designated N, G1 and G2, and
      (2) all vaccinia virus polypeptides necessary for replication of said virus in a cell derived from said human, but not a functional thymidine kinase; and
    (b) a pharmaceutically-acceptable carrier, excipient or diluent, and
  (ii) administering said vaccine formulation to said human, wherein a single dose of said vaccine formulation comprises $5 \times 10^5$ to $7 \times 10^7$ plaque forming units of vaccinia virus.

16. The method according to claim 15, wherein the nucleotide sequence encoding said G1 polypeptide and said G2 polypeptide is operably linked to the vaccinia virus 7.5 kD promoter, and wherein the nucleotide sequence encoding said N polypeptide is operably linked to the vaccinia virus 11 kD promoter.

17. The method according to claim 16, wherein said G1 has the sequence (SEQ ID NO: 1):

MET GLY ILE TRP LYS TRP LEU VAL MET ALA SER LEU VAL TRP PRO VAL LEU THR LEU ARG ASN VAL TYR

ASP MET LYS ILE GLU CYS PRO HIS THR VAL SER PHE GLY GLU ASN SER VAL ILE GLY TYR VAL GLU LEU

PRO PRO VAL PRO LEU ALA ASP THR ALA GLN MET VAL PRO GLU SER SER CYS ASN MET ASP ASN HIS GLN

SER LEU ASN THR ILE THR LYS TYR THR GLN VAL SER TRP ARG GLY LYS ALA ASP GLN SER GLN SER SER

GLN ASN SER PHE GLU THR VAL SER THR GLU VAL ASP LEU LYS GLY THR CYS VAL LEU LYS HIS LYS MET

VAL GLU GLU SER TYR ARG SER ARG LYS SER VAL THR CYS TYR ASP LEU SER CYS ASN SER THR TYR CYS

LYS PRO THR LEU TYR MET ILE VAL PRO ILE HIS ALA CYS ASN MET LYS SER CYS LEU ILE ALA LEU GLY

PRO TYR ARG VAL GLN VAL VAL TYR GLU ARG SER TYR CYS MET THR GLY VAL LEU ILE GLU GLY LYS CYS

PHE VAL PRO ASP GLN SER VAL VAL SER ILE ILE LYS HIS GLY ILE PHE ASP ILE ALA SER VAL HIS ILE VAL

CYS PHE PHE VAL ALA VAL LYS GLY ASN THR TYR LYS ILE PHE GLU GLN VAL LYS LYS SER PHE GLU SER

THR CYS ASN ASP THR GLU ASN LYS VAL GLN GLY TYR TYR ILE CYS ILE VAL GLY ASN SER ALA PRO ILE

TYR VAL PRO THR LEU ASP ASP PHE ARG SER MET GLU ALA PHE THR GLY ILE PHE ARG SER PRO HIS GLY

GLU ASP HIS ASP LEU ALA GLY GLU GLU ILE ALA SER TYR SER ILE VAL GLY PRO ALA ASN ALA LYS VAL

PRO HIS SER ALA SER SER ASP THR LEU SER LEU ILE ALA TYR SER GLY ILE PRO SER TYR SER SER LEU SER

ILE LEU THR SER SER THR GLU ALA LYS HIS VAL PHE SER PRO GLY LEU PHE PRO LYS LEU ASN HIS THR ASN

CYS ASP LYS SER ALA ILE PRO LEU ILE TRP THR GLY MET ILE ASP LEU PRO GLY TYR TYR GLU ALA VAL HIS

PRO CYS THR VAL PHE CYS VAL LEU SER GLY PRO GLY ALA SER CYS GLU ALA PHE SER GLU GLY GLY ILE

PHE ASN ILE THR SER PRO MET CYS LEU VAL SER LYS GLN ASN ARG PHE ARG LEU THR GLU GLN GLN VAL

ASN PHE VAL CYS GLN ARG VAL ASP MET ASP ILE VAL VAL TYR CYS ASN GLY GLN ARG LYS VAL ILE LEU

THR LYS THR LEU VAL ILE GLY GLN CYS ILE TYR THR ILE THR SER LEU PHE SER LEU LEU PRO GLY VAL

-continued

ALA HIS SER ILE ALA VAL GLU LEU CYS VAL PRO GLY PHE HIS GLY TRP ALA THR ALA ALA LEU LEU VAL

THR PHE CYS PHE GLY TRP VAL LEU ILE PRO ALA ILE THR PHE ILE ILE LEU THR VAL LEU LYS PHE ILE ALA

ASN ILE PHE HIS THR SER ASN GLN GLU ASN ARG LEU LYS SER VAL LEU ARG LYS ILE LYS GLU GLU PHE

GLU LYS THR LYS GLY SER MET VAL CYS ASP VAL CYS LYS TYR GLU CYS GLU THR TYR LYS GLU LEU LYS

ALA HIS GLY VAL SER CYS PRO GLN SER GLN CYS PRO TYR CYS PHE THR HIS CYS GLU PRO THR GLU ALA

ALA PHE GLN ALA HIS TYR LYS VAL CYS GLN VAL THR HIS ARG PHE ARG ASP ASP LEU LYS LYS THR VAL
THR PRO GLN ASN PHE THR PRO GLY CYS TYR ARG THR LEU ASN LEU PHE ARG TYR LYS SER ARG CYS TYR
ILE PHE THR MET TRP ILE PHE LEU LEU VAL LEU GLU SER ILE LEU TRP ALA ALA SER ALA, said G2 has the sequence (SEQ ID NO: 2):

SER GLU THR PRO LEU THR PRO VAL TRP ASN ASP ASN ALA HIS GLY VAL GLY SER VAL PRO MET HIS THR
ASP LEU GLU LEU ASP PHE SER LEU THR SER SER SER LYS TYR THR TYR ARG ARG LYS LEU THR ASN PRO
LEU GLU GLU ALA GLN SER ILE ASP LEU HIS ILE GLU ILE GLU GLU GLN THR ILE GLY VAL ASP VAL HIS ALA
LEU GLY HIS TRP PHE ASP GLY ARG LEU ASN LEU LYS THR SER PHE HIS CYS TYR GLY ALA CYS THR LYS
TYR GLU TYR PRO TRP HIS THR ALA LYS CYS HIS TYR GLU ARG ASP TYR GLN TYR GLU THR SER TRP GLY
CYS ASN PRO SER ASP CYS PRO GLY VAL GLY THR GLY CYS THR ALA CYS GLY LEU TRY LEU ASP GLN LEU
LYS PRO VAL GLY SER ALA TYR LYS ILE ILE THR ILE ARG TYR SER ARG ARG VAL CYS VAL GLN PHE GLY
GLU GLU ASN LEU CYS LYS ILE ILE ASP MET ASN ASP CYS PHE VAL SER ARG HIS VAL LYS VAL CYS ILE ILE
GLY THR VAL SER LYS PHE SER GLN GLY ASP THR LEU LEU PHE PHE GLY PRO LEU GLU GLY GLY GLY LEU
ILE PHE LYS HIS TRP CYS THR SER THR CYS GLN PHE GLY ASP PRO GLY ASP ILE MET SER PRO ARG ASP LYS
GLY PHE LEU CYS PRO GLU PHE PRO GLY SER PHE ARG LYS LYS CYS ASN PHE ALA THR THR PRO ILE CYS
GLU TYR ASP GLY ASN MET VAL SER GLY TYR LYS LYS VAL MET ALA THR ILE ASP SER PHE GLN SER PHE
ASN THR SER THR MET HIS PHE THR ASP GLU ARG ILE GLU TRP LYS ASP PRO ASP GLY MET LEU ARG ASP
HIS ILE ASN ILE LEU VAL THR LYS ASP ILE ASP PHE ASP ASN LEU GLY GLU ASN PRO CYS LYS ILE GLY LEU
GLN THR SER SER ILE GLU GLY ALA TRP GLY SER GLY VAL GLY PHE THR LEU THR CYS LEU VAL SER LEU
THR GLU CYS PRO THR PHE LEU THR SER ILE LYS ALA CYS ASP LYS ALA ILE CYS TYR GLY ALA GLU SER
VAL THR LEU THR ARG GLY GLN ASN THR VAL LYS VAL SER GLY LYS GLY GLY HIS SER GLY SER THR PHE
ARG CYS CYS HIS GLY GLU ASP CYS SER GLN ILE GLY LEU HIS ALA ALA ALA PRO HIS LEU ASP LYS VAL ASN
GLY ILE SER GLU ILE GLU ASN SER LYS VAL TYR ASP ASP GLY ALA PRO GLN CYS GLY ILE LYS CYS TRP PHE
VAL LYS SER GLY GLU TRP ILE SER GLY ILE PHE SER GLY ASN TRP ILE VAL LEU ILE VAL LEU CYS VAL PHE
LEU LEU PHE SER LEU VAL LEU LEU SER ILE LEU CYS PRO VAL ARG LYS HIS LYS LYS SER and said N has the sequence (SEQ ID NO: 3):

MET ALA THR MET GLU GLU LEU GLN ARG GLU ILE ASN ALA HIS GLU GLY GLN LEU VAL ILE ALA ARG GLN
LYS VAL ARG ASP ALA GLU LYS GLN TYR GLU LYS ASP PRO ASP GLU LEU ASN LYS ARG THR LEU THR ASP
ARG GLU GLY VAL ALA VAL SER ILE GLN ALA LYS ILE ASP GLU LEU LYS ARG GLN LEU ALA ASP ARG ILE
ALA THR GLY LYS ASN LEU GLY LYS GLU GLN ASP PRO THR GLY VAL GLU PRO GLY ASP HIS LEU LYS GLU
ARG SER MET LEU SER TYR GLY ASN VAL LEU ASP LEU ASN HIS LEU ASP ILE ASP GLU PRO THR GLY GLN
THR ALA ASP TRP LEU SER ILE ILE VAL TYR LEU THR SER PHE VAL VAL PRO ILE LEU LEU LYS ALA LEU TYR
MET LEU THR THR ARG GLY ARG GLN THR THR LYS ASP ASN LYS GLY THR ARG ILE ARG PHE LYS ASP ASP
SER SER PHE GLU ASP VAL ASN GLY ILE ARG LYS PRO LYS HIS LEU TYR VAL SER LEU PRO ASN ALA GLN

SER SER MET LYS ALA GLU GLU ILE THR PRO GLY ARG TYR ARG THR ALA VAL CYS GLY LEU TYR PRO ALA

GLN ILE LYS ALA ARG GLN MET ILE SER PRO VAL MET SER VAL ILE GLY PHE LEU ALA LEU ALA LYS ASP

TRP SER ASP ARG ILE GLU GLN TRP LEU ILE GLU PRO CYS LYS LEU LEU PRO ASP THR ALA ALA VAL SER LEU

LEU GLY GLY PRO ALA THR ASN ARG ASP TYR LEU ARG GLN ARG GLN VAL ALA LEU GLY ASN MET GLU

THR LYS GLU SER LYS ALA ILE ARG GLN HIS ALA GLU ALA ALA GLY CYS SER MET ILE GLU ASP ILE GLU

SER PRO SER SER ILE TRP VAL PHE ALA GLY ALA PRO ASP ARG CYS PRO PRO THR CYS LEU PHE ILE ALA GLY

ILE ALA GLU LEU GLY ALA PHE PHE SER ILE LEU GLN ASP MET ARG ASN THR ILE MET ALA SER LYS THR

VAL GLY THR SER GLU GLU LYS LEU ARG LYS LYS SER SER PHE TYR GLN SER TYR LEU ARG ARG THR GLN

SER MET GLY ILE GLN LEU GLY GLN ARG ILE ILE VAL LEU PHE MET VAL ALA TRP GLY LYS GLU ALA VAL

ASP ASN PHE HIS LEU GLY ASP ASP MET ASP PRO GLU LEU ARG THR LEU ALA GLN SER LEU ILE ASP VAL

LYS VAL LYS GLU ILE SER ASN GLN GLU PRO LEU LYS LEU.

18. The method according to claim 17, wherein said DNA molecule comprises a wild-type vaccinia virus genome with the cDNA of the M and S genomic segments of the Hantaan serotype inserted in the vaccinia virus thymidine kinase coding region.

19. The method according to claim 18, wherein said cDNA comprises the sequence: (SEQ ID NO: 4):

ATG GGG ATA TGG AAG TGG CTA GTG ATG GCC AGT TTA GTA TGG CCT GTT TTG ACA CTG AGA AAT GTC

TAT GAC ATG AAA ATT GAG TGC CCC CAT ACA GTA AGT TTT GGG GAA AAC AGT GTG ATA GGT TAT GTA

GAA TTA CCC CCC GTG CCA TTG GCC GAC ACA GCA CAG ATG GTG CCT GAG AGT TCT TGT AAC ATG GAT

AAT CAC CAA TCG TTG AAT ACA ATA ACA AAA TAT ACC CAA GTA AGT TGG AGA GGA AAG GCT GAT CAG

TCA CAG TCT AGT CAA AAT TCA TTT GAG AGA GTG TCC ACT GAA GTT GAC TTG AAA GGA ACA TGT GTT

CTA AAA CAC AAA ATG GTG GAA GAA TCA TAC CGT AGT AGG AAA TCA GTA ACC TGT TAC GAC CTG TCT

TGC AAT AGC ACT TAC TGC AAG CCA ACA CTA TAC ATG ATT GTA CCA ATT CAT GCA TGC AAT ATG ATG

AAA AGC TGT TTG ATT GCA TTG GGA CCA TAC AGR GTA CAG GTG GTT TAT GAG AGA AGT TAC TGT ATG

ACA GGA GTC CTG ATT GAA GGG AAA TGC TTT GTC CCA GAT CAA AGT GTG GTC AGT ATT ATC AAG CAT

GGG ATC TTT GAT ATT GCA AGT TTT CAT ATT GTA TGT TTC TTT GTT GCA GTT AAA GGG AAT ACT TAT AAA

ATT TTT GAA CAG GTT AAG AAA TCC TTT GAA TCA ACA TGC AAT GAT ACA GAG AAT AAA GTG CAA GGA

TAT TAT ATT TGT ATT GTA GGG GGA AAC TCT GCA CCA ATA TAT GTT CCA ACA CTT GAT GAT TTC AGA

TCC ATG GAA GCA TTT ACA GGA ATC TTC AGA TCA CCA CAT GGG GAA GAT CAT GAT CTG GCT GGA GAA

GAA ATT GCA TCT TAT TCT ATA GTC GGA CCT GCC AAT GCA AAA GTT CCT CAT AGT GCT AGC TCA GAT

ACA TTG AGC TTG ATT GCC TAT TCA GGT ATA CCA TCT TAT TCT TCC CTT AGC ATC CTA ACA AGT TCA ACA

GAA GCT AAG CAT GTA TTC AGC CCT GGG TTG TTC CCA AAA CTT AAT CAC ACA AAT TGT GAT AAA AGT

GCC ATA CCA CTC ATA TGG ACT GGG ATG ATT GAT TTA CCT GGA TAC TAC GAA GCT GTC CAC CCT TGT

ACA GTT TTT TGC GTA TTA TCA GGT CCT GGG GCA TCA TGT GAA GCC TTT TCT GAA GGC GGG ATT TTC

AAC ATA ACC TCT CCC ATG TGC TTA GTG TCA AAA CAA AAT CGA TTC CGG TTA ACA GAA CAG CAA GTG

AAT TTT GTG TGT CAG CGA GTG GAC ATG GAC ATT GTT GTG TAC TGA AAC GGG CAG AGG AAA GTA ATA

TTA ACA AAA ACT CTA GTT ATT GGA CAG TGT ATA TAT ACT ATA ACA AGC TTA XXX TCA TTA CTA CCT

GGA GTA GCA CAT TCT ATT GCT GTT GAA TTG TGT GTA CCT GGG TTC ATG GTT GGG CCA CAG CTG CT

CTG CTT GTT ACA TTC TGT TTC GGA TGG GTT CTT ATA CCA GCA ATT ACA TTT ATC ATA CTA ACA GTC CTA

AAG TTC ATT GCT AAT AAT TTT CAC ACA AGT AAT CAA GAG AAT AGG CTA AAA TCA GTA CTT AGA AAG

ATA AAG GAA GAG TTT GAA AAA ACA AAA GGC TCA ATG GTA TGT GAT GTC TGC AAG TAT GAG TGT GAA

ACA TAT AAA GAA TTA AAG GCA CAC GGG GTA TCA TGC CCC CAA TCT CAA TGT CCT TAC TGT TTT ACT

CAT TGT GAA CCT ACA GAA GCA GCA TTC CCA GTC CAT TAC AAG GTA TGC CAA GTT ACT CAC AGA TTC

AGG GAT GAT CTA AAG AAA ACT GTT ACT CCT CAA AAT TTT ACA CCA GGA TGT TAC CGG ACA CTA AAT

TTA TTT AGA TAC AAA AGC AGG TGC TAC ATC TTT ACA ATG TGG ATA TTT CTT CTT GTC TTA GAA TCC ATA

CTG TGG GCT GCA AGT GCA TCA GAG ACA CCA TTA ACT CCT GTC TGG AAT GAC AAT GCC CAT GGG GTA

GGT TCT GTT CCT ATG CAT ACA GAT TTA GAG CTT GAT TTC TCT TTA ACA TCC AGT TCC AAG TAT ACA TAC

CGT AGG AAG TTA ACA AAC CCA CTT GAG GAA GCA CAA TCC ATT GAC CTA CAT ATT GAA ATA GAA GAA

CAG ACA ATT GGT GTT GAT GTG CAT GCT CTA GGA CAC TGG TTT GAT GGT CGT CTT AAC CTT AAA ACA

TCC TTT CAC TGT TAT GGT GCT TGT ACA AAG TAT GAA TAC CCT TGG CAT ACT GCA AAG TGC CAT TAT

GAA AGA GAT TAC CAA TAT GAA ACG AGC TGG GGT TGT AAT CCA TCA GAT TGT CCT GGG GTG GGC ACA

GGC TGT ACA GCA TGT GGT TTA TAC CTA GAT CAA CTG AAA CCA GTT GGT AGT GCT TAT AAA ATT ATC

ACA ATA AGG TAC AGC AGG AGA GTC TGT GTT CAG TTT GGG GAG GAA AAC CTT TGT AAG ATA ATA GAG

ATG AAT GAT TGT TTT GTA TCT AGG CAT GTT AAG GTC TGC ATA ATT GGT ACA GTA TCT AAA TTC TCT CAG

GGT GAT ACC TTA TTG TTT TTT GGA CCG CTT GAA GGT GGT GGT CTA ATA TTT AAA CAC TGG TGT ACA

TCC ACA TGT CAA TTT GGT GAC CCA GGA GAT ATC ATG AGT CCA AGA GAC AAA GGT TTT TTA TGC CCT

GAG TTT CCA GGT AGT TTC AGG AAG AAA TGC AAC TTT GCT ACT ACC CCT ATT TGT GAG TAT GAT GGA

AAT ATG GTC TCA GGT TAC AAG AAA GTG ATG GCG ACA ATT GAT TCC TTC CAA TCT TTT AAT ACA AGC

ACT ATG CAC TTC ACT GAT GAA AGG ATA GAG TGG AAA GAC CCT GAT GGA ATG CTA AGG GAC CAT ATA

AAC ATT TTA GTA ACG AAG GAC ATT GAC TTT GAT AAC CTT GGT GAA AAT CCT TGC AAA ATT GGC CTA

CAA ACA TCT TCT ATT GAG GGG GCC TGG GGT TCT GGT GTG GGG TTC ACA TTA ACA TGT CTG GTA TCA

CTA ACA GAA TGT CCT ACC TTT TTG ACC TCA ATA AAG GCT TGT GAT AAG GCT ATC TGT TAT GGT GCA

GAG AGT GTA ACA TTG ACA AGA GGA CAA AAT ACA GTC AAG GTA TCA GGG AAA GGT GGC CAT AGT GGT

TCA ACA TTT AGG TGT TGC ATG GGG AGG ACT GTT TCA CAA ATT GGA CTC CAT GCT GCT GCA CCT CAC

CTT GAC AAG GTA AAT GGG ATT TCT GAG ATA GAA AAT AGT AAA GTA TAT GAT GAT GGG GCA CCG CAA

TGT GGG ATA AAA TGT TGG TTT GTT AAA TCA GGG GAA TGG ATT TCA GGG ATA TTC AGT GGT AAT TGG

ATT GTA CTC ATT GTC CTC TGT GTA TTT CTA TTG TTC TCC TTG GTT TTA CTA AGC ATT CTC TGT CCC GTA

AGG AAG CAT AAA AAA TCA and (SEQ ID NO: 5):

ATG GCA ACT ATG GAG GAA TTA CAG AGG GAA ATC AAT GCC CAT GAG GGT CAA TTA GTG ATA GCC AGG
CAG AAG GTG AGG GAT GCA GAA AAA CAG TAT GAA AAG GAT CCA GAT GAG TTG AAC AAG AGA ACA TTA
ACT GAC CGA GAG GGC GTT GCA GTA TCT ATC CAG GCA AAA ATT GAT GAG TTA AAA AGG CAA CTG GCA
GAT AGG ATT GCA ACT GGG AAA AAC CTT GGG AAG GAA CAA GAT CCA ACA GGG GTG GAG CCT GGA GAC
CAT CTG AAA GAG AGG TCA ATG CTC AGT TAT GGT AAT GTG CTG GAT TTA AAC CAT TTG GAT ATT GAT
GAA CCT ACA GGA CAG ACA GCA GAC TGG CTG AGC ATC ATC GTC TAT CTT ACA TCC TTT GTC GTC CCG
ATA CTT CTG AAA GTC CTG TAT ATG TTG ACA ACA AGG GGG AGG CAA ACT ACC AAG GAT AAT AAA GGG
ACC CGG ATT CGA TTT AAG GAT GAT AGC TCG TTC GAG GAT GTT AAC GGT ATC CGG AAA CCA AAA CAT
CTT TAC GTG TCC TTG CCA AAT GCA CAG TCA AGC ATG AAG GCA GAA GAG ATT ACA CCT GGT AGA TAT
AGA ACA GCA GTC TGT GGG CTC TAC CCT GCA CAG ATT AAG GCA CGG CAG ATG ATC AGT CCA GTT ATG

-continued

```
AGT GTA ATT GGT TTT CTA GCA TTA GCA AAG GAC TGG AGT GAT CGT ATC GAA CAA TGG TTA ATT GAA
CCT TGC AAG CTT CTT CCA GAT ACA GCA GCA GTT AGC CTC CTC GGT GGT CCT GCA ACA AAC AGG GAC
TAC TTA CGG CAG CGG CAA GTG GCA TTA GGC AAT ATG GAG ACA AAG GAG TCA AAG GCT ATA CGC AG
CAT GCA GAA GCA GCT GGC TGT AGC ATG ATT GAA GAT ATT GAG TCA CCA TCA TCA ATA TGG GTT TTT
GCT GGA GCA CCA GAC CGT TGT CCA CCA ACA TGT TTG TTT ATA GCA GGT ATT GCT GAG CTT GGG GCA
TTT TTT TCC ATC CTG CAG GAC ATG CGA AAT ACA ATC ATG GCA TCT AAG ACR GTT GGA ACA TCT GAG
GAG AAG CTA CGG AAG AAA TCA TCA TTT TAT CAG TCC TAC CTC AGA AGG ACA CAA TCA ATG GGG ATA
CAA CTA GGC CAG AGA ATT ATT GTG CTC TTC ATG GTT GCC TGG GGA AAG GAG GCT GTG GAC AAC TTC
CAC TTA GGG GAT GAT ATG GAT CCT GAG CTA AGG ACA CTG GCA CAG AGC TTG ATT GAT GTC AAA GTG
AAG GAA ATC TCC AAC CAA GAG CCT TTG AAA CTC.
```

20. The method according to claim 15, wherein said single dose comprises $5 \times 10^5$ to $7 \times 10^7$ plaque-forming units.

21. The method according to claim 15, wherein said single dose comprises $5 \times 10^5$ to $1 \times 10^6$ plaque-forming units.

22. The method according to claim 15, wherein said single dose comprises $5 \times 10^5$ plaque-forming units.

23. The method according to claim 15, wherein said single dose comprises $3.4 \times 10^7$ plaque-forming units.

24. The method according to claim 23, wherein said pharmaceutically-acceptable carrier, excipient or diluent further comprises lactose and human serum albumin.

25. The method according to claim 24, wherein said lactose is 5% (w/v) of said formulation and said human serum albumin is 1% (w/v) of said formulation.

26. The method according to claim 25, wherein said formulation further comprises neomycin of no more than 25 µg per single dose of said formulation.

27. The method according to claim 26, wherein said single dose of said formulation is in a volume of 0.1 to 1.0 ml.

28. The method according to claim 27, wherein said administering is by a route selected from the group consisting of subcutaneous, intramuscular and intradermal.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 647 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met  Gly  Ile  Trp  Lys  Trp  Leu  Val  Met  Ala  Ser  Leu  Val  Trp  Pro  Val
 1              5                        10                       15

Leu  Thr  Leu  Arg  Asn  Val  Tyr  Asp  Met  Lys  Ile  Glu  Cys  Pro  His  Thr
              20                        25                       30

Val  Ser  Phe  Gly  Glu  Asn  Ser  Val  Ile  Gly  Tyr  Val  Glu  Leu  Pro  Pro
              35                        40                       45

Val  Pro  Leu  Ala  Asp  Thr  Ala  Gln  Met  Val  Pro  Glu  Ser  Ser  Cys  Asn
         50                   55                       60

Met  Asp  Asn  His  Gln  Ser  Leu  Asn  Thr  Ile  Thr  Lys  Tyr  Thr  Gln  Val
65                            70                       75                  80

Ser  Trp  Arg  Gly  Lys  Ala  Asp  Gln  Ser  Gln  Ser  Ser  Gln  Asn  Ser  Phe
                   85                            90                       95

Glu  Thr  Val  Ser  Thr  Glu  Val  Asp  Leu  Lys  Gly  Thr  Cys  Val  Leu  Lys
```

|  |  |  |  |  | 100 |  |  |  | 105 |  |  |  | 110 |  |  |
|---|---|---|---|---|---|---|---|---|---|---|---|---|---|---|---|
| His | Lys | Met | Val | Glu | Glu | Ser | Tyr | Arg | Ser | Arg | Lys | Ser | Val | Thr | Cys |
|  |  | 115 |  |  |  |  | 120 |  |  |  | 125 |  |  |  |  |
| Tyr | Asp | Leu | Ser | Cys | Asn | Ser | Thr | Tyr | Cys | Lys | Pro | Thr | Leu | Tyr | Met |
|  | 130 |  |  |  | 135 |  |  |  |  | 140 |  |  |  |  |  |
| Ile | Val | Pro | Ile | His | Ala | Cys | Asn | Met | Met | Lys | Ser | Cys | Leu | Ile | Ala |
| 145 |  |  |  |  | 150 |  |  |  |  | 155 |  |  |  |  | 160 |
| Leu | Gly | Pro | Tyr | Arg | Val | Gln | Val | Val | Tyr | Glu | Arg | Ser | Tyr | Cys | Met |
|  |  |  |  | 165 |  |  |  |  | 170 |  |  |  |  | 175 |  |
| Thr | Gly | Val | Leu | Ile | Glu | Gly | Lys | Cys | Phe | Val | Pro | Asp | Gln | Ser | Val |
|  |  |  | 180 |  |  |  |  | 185 |  |  |  |  | 190 |  |  |
| Val | Ser | Ile | Ile | Lys | His | Gly | Ile | Phe | Asp | Ile | Ala | Ser | Val | His | Ile |
|  |  | 195 |  |  |  |  | 200 |  |  |  |  | 205 |  |  |  |
| Val | Cys | Phe | Phe | Val | Ala | Val | Lys | Gly | Asn | Thr | Tyr | Lys | Ile | Phe | Glu |
|  | 210 |  |  |  |  | 215 |  |  |  |  | 220 |  |  |  |  |
| Gln | Val | Lys | Lys | Ser | Phe | Glu | Ser | Thr | Cys | Asn | Asp | Thr | Glu | Asn | Lys |
| 225 |  |  |  |  | 230 |  |  |  |  | 235 |  |  |  |  | 240 |
| Val | Gln | Gly | Tyr | Tyr | Ile | Cys | Ile | Val | Gly | Asn | Ser | Ala | Pro | Ile | Tyr |
|  |  |  |  | 245 |  |  |  |  | 250 |  |  |  |  | 255 |  |
| Val | Pro | Thr | Leu | Asp | Asp | Phe | Arg | Ser | Met | Glu | Ala | Phe | Thr | Gly | Ile |
|  |  |  | 260 |  |  |  |  | 265 |  |  |  |  | 270 |  |  |
| Phe | Arg | Ser | Pro | His | Gly | Glu | Asp | His | Asp | Leu | Ala | Gly | Glu | Glu | Ile |
|  |  | 275 |  |  |  |  | 280 |  |  |  |  | 285 |  |  |  |
| Ala | Ser | Tyr | Ser | Ile | Val | Gly | Pro | Ala | Asn | Ala | Lys | Val | Pro | His | Ser |
|  | 290 |  |  |  |  | 295 |  |  |  |  | 300 |  |  |  |  |
| Ala | Ser | Ser | Asp | Thr | Leu | Ser | Leu | Ile | Ala | Tyr | Ser | Gly | Ile | Pro | Ser |
| 305 |  |  |  |  | 310 |  |  |  |  | 315 |  |  |  |  | 320 |
| Tyr | Ser | Ser | Leu | Ser | Ile | Leu | Thr | Ser | Ser | Thr | Glu | Ala | Lys | His | Val |
|  |  |  |  | 325 |  |  |  |  | 330 |  |  |  |  | 335 |  |
| Phe | Ser | Pro | Gly | Leu | Phe | Pro | Lys | Leu | Asn | His | Thr | Asn | Cys | Asp | Lys |
|  |  |  | 340 |  |  |  |  | 345 |  |  |  |  | 350 |  |  |
| Ser | Ala | Ile | Pro | Leu | Ile | Trp | Thr | Gly | Met | Ile | Asp | Leu | Pro | Gly | Tyr |
|  |  | 355 |  |  |  |  | 360 |  |  |  |  | 365 |  |  |  |
| Tyr | Glu | Ala | Val | His | Pro | Cys | Thr | Val | Phe | Cys | Val | Leu | Ser | Gly | Pro |
|  | 370 |  |  |  |  | 375 |  |  |  |  | 380 |  |  |  |  |
| Gly | Ala | Ser | Cys | Glu | Ala | Phe | Ser | Glu | Gly | Gly | Ile | Phe | Asn | Ile | Thr |
| 385 |  |  |  |  | 390 |  |  |  |  | 395 |  |  |  |  | 400 |
| Ser | Pro | Met | Cys | Leu | Val | Ser | Lys | Gln | Asn | Arg | Phe | Arg | Leu | Thr | Glu |
|  |  |  |  | 405 |  |  |  |  | 410 |  |  |  |  | 415 |  |
| Gln | Gln | Val | Asn | Phe | Val | Cys | Gln | Arg | Val | Asp | Met | Asp | Ile | Val | Val |
|  |  |  | 420 |  |  |  |  | 425 |  |  |  |  | 430 |  |  |
| Tyr | Cys | Asn | Gly | Gln | Arg | Lys | Val | Ile | Leu | Thr | Lys | Thr | Leu | Val | Ile |
|  |  | 435 |  |  |  |  | 440 |  |  |  |  | 445 |  |  |  |
| Gly | Gln | Cys | Ile | Tyr | Thr | Ile | Thr | Ser | Leu | Phe | Ser | Leu | Leu | Pro | Gly |
|  | 450 |  |  |  |  | 455 |  |  |  |  | 460 |  |  |  |  |
| Val | Ala | His | Ser | Ile | Ala | Val | Glu | Leu | Cys | Val | Pro | Gly | Phe | His | Gly |
| 465 |  |  |  |  | 470 |  |  |  |  | 475 |  |  |  |  | 480 |
| Trp | Ala | Thr | Ala | Ala | Leu | Leu | Val | Thr | Phe | Cys | Phe | Gly | Trp | Val | Leu |
|  |  |  |  | 485 |  |  |  |  | 490 |  |  |  |  | 495 |  |
| Ile | Pro | Ala | Ile | Thr | Phe | Ile | Ile | Leu | Thr | Val | Leu | Lys | Phe | Ile | Ala |
|  |  |  | 500 |  |  |  |  | 505 |  |  |  |  | 510 |  |  |
| Asn | Ile | Phe | His | Thr | Ser | Asn | Gln | Glu | Asn | Arg | Leu | Lys | Ser | Val | Leu |
|  |  | 515 |  |  |  |  | 520 |  |  |  |  | 525 |  |  |  |

```
Arg  Lys  Ile  Lys  Glu  Glu  Phe  Glu  Lys  Thr  Lys  Gly  Ser  Met  Val  Cys
     530                      535                 540

Asp  Val  Cys  Lys  Tyr  Glu  Cys  Glu  Thr  Tyr  Lys  Glu  Leu  Lys  Ala  His
545                      550                 555                           560

Gly  Val  Ser  Cys  Pro  Gln  Ser  Gln  Cys  Pro  Tyr  Cys  Phe  Thr  His  Cys
               565                      570                           575

Glu  Pro  Thr  Glu  Ala  Ala  Phe  Gln  Ala  His  Tyr  Lys  Val  Cys  Gln  Val
               580                      585                      590

Thr  His  Arg  Phe  Arg  Asp  Asp  Leu  Lys  Lys  Thr  Val  Thr  Pro  Gln  Asn
          595                      600                      605

Phe  Thr  Pro  Gly  Cys  Tyr  Arg  Thr  Leu  Asn  Leu  Phe  Arg  Tyr  Lys  Ser
          610                 615                      620

Arg  Cys  Tyr  Ile  Phe  Thr  Met  Trp  Ile  Phe  Leu  Leu  Val  Leu  Glu  Ser
625                      630                      635                      640

Ile  Leu  Trp  Ala  Ala  Ser  Ala
                    645
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Ser  Glu  Thr  Pro  Leu  Thr  Pro  Val  Trp  Asn  Asp  Asn  Ala  His  Gly  Val
1                   5                     10                          15

Gly  Ser  Val  Pro  Met  His  Thr  Asp  Leu  Glu  Leu  Asp  Phe  Ser  Leu  Thr
               20                     25                          30

Ser  Ser  Ser  Lys  Tyr  Thr  Tyr  Arg  Arg  Lys  Leu  Thr  Asn  Pro  Leu  Glu
               35                     40                     45

Glu  Ala  Gln  Ser  Ile  Asp  Leu  His  Ile  Glu  Ile  Glu  Glu  Gln  Thr  Ile
     50                     55                     60

Gly  Val  Asp  Val  His  Ala  Leu  Gly  His  Trp  Phe  Asp  Gly  Arg  Leu  Asn
65                      70                     75                          80

Leu  Lys  Thr  Ser  Phe  His  Cys  Tyr  Gly  Ala  Cys  Thr  Lys  Tyr  Glu  Tyr
               85                     90                          95

Pro  Trp  His  Thr  Ala  Lys  Cys  His  Tyr  Glu  Arg  Asp  Tyr  Gln  Tyr  Glu
               100                    105                         110

Thr  Ser  Trp  Gly  Cys  Asn  Pro  Ser  Asp  Cys  Pro  Gly  Val  Gly  Thr  Gly
          115                    120                    125

Cys  Thr  Ala  Cys  Gly  Leu  Tyr  Leu  Asp  Gln  Leu  Lys  Pro  Val  Gly  Ser
     130                    135                    140

Ala  Tyr  Lys  Ile  Ile  Thr  Ile  Arg  Tyr  Ser  Arg  Arg  Val  Cys  Val  Gln
145                      150                    155                         160

Phe  Gly  Glu  Glu  Asn  Leu  Cys  Lys  Ile  Ile  Asp  Met  Asn  Asp  Cys  Phe
                    165                    170                    175

Val  Ser  Arg  His  Val  Lys  Val  Cys  Ile  Ile  Gly  Thr  Val  Ser  Lys  Phe
               180                    185                    190

Ser  Gln  Gly  Asp  Thr  Leu  Leu  Phe  Phe  Gly  Pro  Leu  Glu  Gly  Gly  Gly
          195                    200                    205

Leu  Ile  Phe  Lys  His  Trp  Cys  Thr  Ser  Thr  Cys  Gln  Phe  Gly  Asp  Pro
     210                    215                    220

Gly  Asp  Ile  Met  Ser  Pro  Arg  Asp  Lys  Gly  Phe  Leu  Cys  Pro  Glu  Phe
```

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Pro | Gly | Ser | Phe | Arg | Lys | Lys | Cys | Asn | Phe | Ala | Thr | Thr | Pro | Ile | Cys |
|     |     |     |     | 245 |     |     |     |     | 250 |     |     |     |     | 255 |     |
| Glu | Tyr | Asp | Gly | Asn | Met | Val | Ser | Gly | Tyr | Lys | Lys | Val | Met | Ala | Thr |
|     |     |     | 260 |     |     |     |     | 265 |     |     |     | 270 |     |     |     |
| Ile | Asp | Ser | Phe | Gln | Ser | Phe | Asn | Thr | Ser | Thr | Met | His | Phe | Thr | Asp |
|     |     | 275 |     |     |     |     | 280 |     |     |     | 285 |     |     |     |     |
| Glu | Arg | Ile | Glu | Trp | Lys | Asp | Pro | Asp | Gly | Met | Leu | Arg | Asp | His | Ile |
|     | 290 |     |     |     |     | 295 |     |     |     | 300 |     |     |     |     |     |
| Asn | Ile | Leu | Val | Thr | Lys | Asp | Ile | Asp | Phe | Asp | Asn | Leu | Gly | Glu | Asn |
| 305 |     |     |     |     | 310 |     |     |     | 315 |     |     |     |     | 320 |     |
| Pro | Cys | Lys | Ile | Gly | Leu | Gln | Thr | Ser | Ser | Ile | Glu | Gly | Ala | Trp | Gly |
|     |     |     |     | 325 |     |     |     |     | 330 |     |     |     | 335 |     |     |
| Ser | Gly | Val | Gly | Phe | Thr | Leu | Thr | Cys | Leu | Val | Ser | Leu | Thr | Glu | Cys |
|     |     |     | 340 |     |     |     |     | 345 |     |     |     | 350 |     |     |     |
| Pro | Thr | Phe | Leu | Thr | Ser | Ile | Lys | Ala | Cys | Asp | Lys | Ala | Ile | Cys | Tyr |
|     |     | 355 |     |     |     |     | 360 |     |     |     | 365 |     |     |     |     |
| Gly | Ala | Glu | Ser | Val | Thr | Leu | Thr | Arg | Gly | Gln | Asn | Thr | Val | Lys | Val |
|     | 370 |     |     |     |     | 375 |     |     |     | 380 |     |     |     |     |     |
| Ser | Gly | Lys | Gly | Gly | His | Ser | Gly | Ser | Thr | Phe | Arg | Cys | Cys | His | Gly |
| 385 |     |     |     |     | 390 |     |     |     | 395 |     |     |     |     | 400 |     |
| Glu | Asp | Cys | Ser | Gln | Ile | Gly | Leu | His | Ala | Ala | Ala | Pro | His | Leu | Asp |
|     |     |     |     | 405 |     |     |     |     | 410 |     |     |     | 415 |     |     |
| Lys | Val | Asn | Gly | Ile | Ser | Glu | Ile | Glu | Asn | Ser | Lys | Val | Tyr | Asp | Asp |
|     |     |     | 420 |     |     |     |     | 425 |     |     |     | 430 |     |     |     |
| Gly | Ala | Pro | Gln | Cys | Gly | Ile | Lys | Cys | Trp | Phe | Val | Lys | Ser | Gly | Glu |
|     |     | 435 |     |     |     |     | 440 |     |     |     | 445 |     |     |     |     |
| Trp | Ile | Ser | Gly | Ile | Phe | Ser | Gly | Asn | Trp | Ile | Val | Leu | Ile | Val | Leu |
|     | 450 |     |     |     |     | 455 |     |     |     | 460 |     |     |     |     |     |
| Cys | Val | Phe | Leu | Leu | Phe | Ser | Leu | Val | Leu | Leu | Ser | Ile | Leu | Cys | Pro |
| 465 |     |     |     |     | 470 |     |     |     | 475 |     |     |     |     | 480 |     |
| Val | Arg | Lys | His | Lys | Lys | Ser |     |     |     |     |     |     |     |     |     |
|     |     |     |     | 485 |     |     |     |     |     |     |     |     |     |     |     |

( 2 ) INFORMATION FOR SEQ ID NO:3:

( i ) SEQUENCE CHARACTERISTICS:
        ( A ) LENGTH: 429 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

| Met | Ala | Thr | Met | Glu | Glu | Leu | Gln | Arg | Glu | Ile | Asn | Ala | His | Glu | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Leu | Val | Ile | Ala | Arg | Gln | Lys | Val | Arg | Asp | Ala | Glu | Lys | Gln | Tyr |
|     |     |     | 20  |     |     |     |     | 25  |     |     |     | 30  |     |     |     |
| Glu | Lys | Asp | Pro | Asp | Glu | Leu | Asn | Lys | Arg | Thr | Leu | Thr | Asp | Arg | Glu |
|     |     | 35  |     |     |     |     | 40  |     |     |     | 45  |     |     |     |     |
| Gly | Val | Ala | Val | Ser | Ile | Gln | Ala | Lys | Ile | Asp | Glu | Leu | Lys | Arg | Gln |
|     | 50  |     |     |     |     | 55  |     |     |     | 60  |     |     |     |     |     |
| Leu | Ala | Asp | Arg | Ile | Ala | Thr | Gly | Lys | Asn | Leu | Gly | Lys | Glu | Gln | Asp |
| 65  |     |     |     |     | 70  |     |     |     | 75  |     |     |     |     | 80  |     |
| Pro | Thr | Gly | Val | Glu | Pro | Gly | Asp | His | Leu | Lys | Glu | Arg | Ser | Met | Leu |
|     |     |     |     | 85  |     |     |     |     | 90  |     |     |     |     | 95  |     |

| Ser | Tyr | Gly | Asn 100 | Val | Leu | Asp | Leu | Asn 105 | His | Leu | Asp | Ile | Asp 110 | Glu | Pro |
|---|---|---|---|---|---|---|---|---|---|---|---|---|---|---|---|
| Thr | Gly | Gln 115 | Thr | Ala | Asp | Trp | Leu 120 | Ser | Ile | Val | Tyr 125 | Leu | Thr | Ser | |
| Phe | Val 130 | Val | Pro | Ile | Leu | Leu 135 | Lys | Ala | Leu | Tyr | Met 140 | Leu | Thr | Thr | Arg |
| Gly 145 | Arg | Gln | Thr | Thr | Lys 150 | Asp | Asn | Lys | Gly | Thr 155 | Arg | Ile | Arg | Phe | Lys 160 |
| Asp | Asp | Ser | Ser | Phe 165 | Glu | Asp | Val | Asn | Gly 170 | Ile | Arg | Lys | Pro | Lys 175 | His |
| Leu | Tyr | Val | Ser 180 | Leu | Pro | Asn | Ala | Gln 185 | Ser | Ser | Met | Lys | Ala 190 | Glu | Glu |
| Ile | Thr | Pro 195 | Gly | Arg | Tyr | Arg | Thr 200 | Ala | Val | Cys | Gly | Leu 205 | Tyr | Pro | Ala |
| Gln | Ile 210 | Lys | Ala | Arg | Gln | Met 215 | Ile | Ser | Pro | Val | Met 220 | Ser | Val | Ile | Gly |
| Phe 225 | Leu | Ala | Leu | Ala | Lys 230 | Asp | Trp | Ser | Asp | Arg 235 | Ile | Glu | Gln | Trp | Leu 240 |
| Ile | Glu | Pro | Cys | Lys 245 | Leu | Leu | Pro | Asp | Thr 250 | Ala | Ala | Val | Ser | Leu 255 | Leu |
| Gly | Gly | Pro | Ala 260 | Thr | Asn | Arg | Asp | Tyr 265 | Leu | Arg | Gln | Arg | Gln 270 | Val | Ala |
| Leu | Gly | Asn 275 | Met | Glu | Thr | Lys | Glu 280 | Ser | Lys | Ala | Ile | Arg 285 | Gln | His | Ala |
| Glu | Ala 290 | Ala | Gly | Cys | Ser | Met 295 | Ile | Glu | Asp | Ile | Glu 300 | Ser | Pro | Ser | Ser |
| Ile 305 | Trp | Val | Phe | Ala | Gly 310 | Ala | Pro | Asp | Arg | Cys 315 | Pro | Pro | Thr | Cys | Leu 320 |
| Phe | Ile | Ala | Gly | Ile 325 | Ala | Glu | Leu | Gly | Ala 330 | Phe | Phe | Ser | Ile | Leu 335 | Gln |
| Asp | Met | Arg | Asn 340 | Thr | Ile | Met | Ala | Ser 345 | Lys | Thr | Val | Gly | Thr 350 | Ser | Glu |
| Glu | Lys | Leu 355 | Arg | Lys | Lys | Ser | Ser 360 | Phe | Tyr | Gln | Ser | Tyr 365 | Leu | Arg | Arg |
| Thr | Gln 370 | Ser | Met | Gly | Ile | Gln 375 | Leu | Gly | Gln | Arg | Ile 380 | Ile | Val | Leu | Phe |
| Met 385 | Val | Ala | Trp | Gly | Lys 390 | Glu | Ala | Val | Asp | Asn 395 | Phe | His | Leu | Gly | Asp 400 |
| Asp | Met | Asp | Pro | Glu 405 | Leu | Arg | Thr | Leu | Ala 410 | Gln | Ser | Leu | Ile | Asp 415 | Val |
| Lys | Val | Lys | Glu 420 | Ile | Ser | Asn | Gln | Glu 425 | Pro | Leu | Lys | Leu | | | |

( 2 ) INFORMATION FOR SEQ ID NO:4:

( i ) SEQUENCE CHARACTERISTICS:
        ( A ) LENGTH: 3401 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ATGGGGATAT GGAAGTGGCT AGTGATGGCC AGTTTAGTAT GGCCTGTTTT GACACTGAGA      60

AATGTCTATG ACATGAAAAT TGAGTGCCCC CATACAGTAA GTTTTGGGGA AAACAGTGTG     120
```

-continued

| | | | | | |
|---|---|---|---|---|---|
|ATAGGTTATG|TAGAATTACC|CCCCGTGCCA|TTGGCCGACA|CAGCACAGAT|GGTGCCTGAG|180|
|AGTTCTTGTA|ACATGGATAA|TCACCAATCG|TTGAATACAA|TAACAAAATA|TACCCAAGTA|240|
|AGTTGGAGAG|GAAAGGCTGA|TCAGTCACAG|TCTAGTCAAA|ATTCATTTGA|GAGAGTGTCC|300|
|ACTGAAGTTG|ACTTGAAAGG|AACATGTGTT|CTAAAACACA|AATGGTGGA|AGAATCATAC|360|
|CGTAGTAGGA|AATCAGTAAC|CTGTTACGAC|CTGTCTTGCA|ATAGCACTTA|CTGCAAGCCA|420|
|ACACTATACA|TGATTGTACC|AATTCATGCA|TGCAATATGA|TGAAAAGCTG|TTTGATTGCA|480|
|TTGGGACCAT|ACAGGTACAG|GTGGTTTATG|AGAGAAGTTA|CTGTATGACA|GGAGTCCTGA|540|
|TTGAAGGGAA|ATGCTTTGTC|CCAGATCAAA|GTGTGGTCAG|TATTATCAAG|CATGGGATCT|600|
|TTGATATTGC|AAGTTTTCAT|ATTGTATGTT|TCTTGTTGC|AGTTAAAGGG|AATACTTATA|660|
|AAATTTTGA|ACAGGTTAAG|AAATCCTTTG|AATCAACATG|CAATGATACA|GAGAATAAAG|720|
|TGCAAGGATA|TTATATTTGT|ATTGTAGGGG|GAAACTCTGC|ACCAATATAT|GTTCCAACAC|780|
|TTGATGATTT|CAGATCCATG|GAAGCATTTA|CAGGAATCTT|CAGATCACCA|CATGGGGAAG|840|
|ATCATGATCT|GGCTGGAGAA|GAAATTGCAT|CTTATTCTAT|AGTCGGACCT|GCCAATGCAA|900|
|AAGTTCCTCA|TAGTGCTAGC|TCAGATACAT|TGAGCTTGAT|TGCCTATTCA|GGTATACCAT|960|
|CTTATTCTTC|CCTTAGCATC|CTAACAAGTT|CAACAGAAGC|TAAGCATGTA|TTCAGCCCTG|1020|
|GGTGTTCCC|AAAACTTAAT|CACACAAATT|GTGATAAAAG|TGCCATACCA|CTCATATGGA|1080|
|CTGGGATGAT|TGATTTACCT|GGATACTACG|AAGCTGTCCA|CCCTTGTACA|GTTTTTTGCG|1140|
|TATTATCAGG|TCCTGGGGCA|TCATGTGAAG|CCTTTTCTGA|AGGCGGGATT|TCAACATAA|1200|
|CCTCTCCCAT|GTGCTTAGTG|TCAAAACAAA|ATCGATTCCG|GTTAACAGAA|CAGCAAGTGA|1260|
|ATTTGTGTG|TCAGCGAGTG|GACATGGACA|TTGTTGTGTA|CTGCAACGGG|CAGAGGAAAG|1320|
|TAATATTAAC|AAAAACTCTA|GTTATTGGAC|AGTGTATATA|TACTATAACA|AGCTTATCAT|1380|
|TACTACCTGG|AGTAGCACAT|TCTATTGCTG|TTGAATTGTG|TGTACCTGGG|TTCCATGGTT|1440|
|GGGCCACAGC|TGCTCTGCTT|GTTACATTCT|GTTTCGGATG|GGTTCTTATA|CCAGCAATTA|1500|
|CATTTATCAT|ACTAACAGTC|CTAAAGTTCA|TTGCTAATAA|TTTTCACACA|AGTAATCAAG|1560|
|AGAATAGGCT|AAAATCAGTA|CTTAGAAAGA|TAAAGGAAGA|GTTTGAAAAA|ACAAAGGCT|1620|
|CAATGGTATG|TGATGTCTGC|AAGTATGAGT|GTGAAACATA|TAAAGAATTA|AAGGCACACG|1680|
|GGGTATCATG|CCCCCAATCT|CAATGTCCTT|ACTGTTTTAC|TCATTGTGAA|CCTACAGAAG|1740|
|CAGCATTCCC|AGTCCATTAC|AAGGTATGCC|AAGTTACTCA|CAGATTCAGG|GATGATCTAA|1800|
|AGAAAACTGT|TACTCCTCAA|AATTTTACAC|CAGGATGTTA|CCGGACACTA|AATTTATTTA|1860|
|GATACAAAAG|CAGGTGCTAC|ATCTTTACAA|TGTGGATATT|TCTTCTTGTC|TTAGAATCCA|1920|
|TACTGTGGGC|TGCAAGTGCA|TCAGAGACAC|CATTAACTCC|TGTCTGGAAT|GACAATGCCC|1980|
|ATGGGGTAGG|TTCTGTTCCT|ATGCATACAG|ATTTAGAGCT|TGATTTCTCT|TTAACATCCA|2040|
|GTTCCAAGTA|TACATACCGT|AGGAAGTTAA|CAAACCCACT|TGAGGAAGCA|CAATCCATTG|2100|
|ACCTACATAT|TGAAATAGAA|GAACAGACAA|TTGGTGTTGA|TGTGCATGCT|CTAGGACACT|2160|
|GGTTTGATGG|TCGTCTTAAC|CTTAAAACAT|CCTTTCACTG|TTATGGTGCT|TGTACAAAGT|2220|
|ATGAATACCC|TTGGCATACT|GCAAAGTGCC|ATTATGAAAG|AGATTACCAA|TATGAAACGA|2280|
|GCTGGGGTTG|TAATCCATCA|GATTGTCCTG|GGTGGGCAC|AGGCTGTACA|GCATGTGGTT|2340|
|TATACCTAGA|TCAACTGAAA|CCAGTTGGTA|GTGCTTATAA|AATTATCACA|ATAAGGTACA|2400|
|GCAGGAGAGT|CTGTGTTCAG|TTTGGGGAGG|AAAACCTTTG|TAAGATAATA|GAGATGAATG|2460|
|ATTGTTTTGT|ATCTAGGCAT|GTTAAGGTCT|GCATAATTGG|TACAGTATCT|AAATTCTCTC|2520|

| | | | | | |
|---|---|---|---|---|---|
|AGGGTGATAC|CTTATTGTTT|TTTGGACCGC|TTGAAGGTGG|TGGTCTAATA|TTTAAACACT|2580|
|GGTGTACATC|CACATGTCAA|TTTGGTGACC|CAGGAGATAT|CATGAGTCCA|AGAGACAAAG|2640|
|GTTTTTTATG|CCCTGAGTTT|CCAGGTAGTT|TCAGGAAGAA|ATGCAACTTT|GCTACTACCC|2700|
|CTATTTGTGA|GTATGATGGA|AATATGGTCT|CAGGTTACAA|GAAAGTGATG|GCGACAATTG|2760|
|ATTCCTTCCA|ATCTTTTAAT|ACAAGCACTA|TGCACTTCAC|TGATGAAAGG|ATAGAGTGGA|2820|
|AAGACCCTGA|TGGAATGCTA|AGGGACCATA|TAAACATTTT|AGTAACGAAG|GACATTGACT|2880|
|TTGATAACCT|TGGTGAAAAT|CCTTGCAAAA|TTGGCCTACA|AACATCTTCT|ATTGAGGGGG|2940|
|CCTGGGGTTC|TGGTGTGGGG|TTCACATTAA|CATGTCTGGT|ATCACTAACA|GAATGTCCTA|3000|
|CCTTTTTGAC|CTCAATAAAG|GCTTGTGATA|AGGCTATCTG|TTATGGTGCA|GAGAGTGTAA|3060|
|CATTGACAAG|AGGACAAAAT|ACAGTCAAGG|TATCAGGGAA|AGGTGGCCAT|AGTGGTTCAA|3120|
|CATTAGGTG|TTGCCATGGG|GAGGACTGTT|CACAAATTGG|ACTCCATGCT|GCTGCACCTC|3180|
|ACCTTGACAA|GGTAAATGGG|ATTTCTGAGA|TAGAAAATAG|TAAAGTATAT|GATGATGGGG|3240|
|CACCGCAATG|TGGGATAAAA|TGTTGGTTTG|TTAAATCAGG|GGAATGGATT|TCAGGGATAT|3300|
|TCAGTGGTAA|TTGGATTGTA|CTCATTGTCC|TCTGTGTATT|TCTATTGTTC|TCCTTGGTTT|3360|
|TACTAAGCAT|TCTCTGTCCC|GTAAGGAAGC|ATAAAAAATC|A||3401|

(2) INFORMATION FOR SEQ ID NO:5:

(i) SEQUENCE CHARACTERISTICS:
  (A) LENGTH: 1286 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:5:

| | | | | | |
|---|---|---|---|---|---|
|ATGGCAACTA|TGGAGGAATT|ACAGAGGGAA|ATCAATGCCC|ATGAGGGTCA|ATTAGTGATA|60|
|GCCAGGCAGA|AGGTGAGGGA|TGCAGAAAAA|CAGTATGAAA|AGGATCCAGA|TGAGTTGAAC|120|
|AAGAGAACAT|TAACTGACCG|AGAGGGCGTT|GCAGTATCTA|TCCAGGCAAA|AATTGATGAG|180|
|TTAAAAAGGC|AACTGGCAGA|TAGGATTGCA|ACTGGGAAAA|ACCTTGGGAA|GGAACAAGAT|240|
|CCAACAGGGG|TGGAGCCTGG|AGACCATCTG|AAAGAGAGGT|CAATGCTCAG|TTATGGTAAT|300|
|GTGCTGGATT|TAAACCATTT|GGATATTGAT|GAACCTACAG|ACAGACAGC|AGACTGGCTG|360|
|AGCATCATCG|TCTATCTTAC|ATCCTTTGTC|GTCCCGATAC|TTCTGAAAGT|CCTGTATATG|420|
|TTGACAACAA|GGGGGAGGCA|AACTACCAAG|GATAATAAAG|GGACCCGGAT|TCGATTTAAG|480|
|GATGATAGCT|CGTTCGAGGA|TGTTAACGGT|ATCCGGAAAC|CAAAACATCT|TTACGTGTCC|540|
|TTGCCAAATG|CACAGTCAAG|CATGAAGGCA|GAAGAGATTA|CACCTGGTAG|ATATAGAACA|600|
|GCAGTCTGTG|GGCTCTACCC|TGCACAGATT|AAGGCACGGC|AGATGATCAG|TCCAGTTATG|660|
|AGTGTAATTG|GTTTTCTAGC|ATTAGCAAAG|GACTGGAGTG|ATCGTATCGA|ACAATGGTTA|720|
|ATTGAACCTT|GCAAGCTTCT|TCCAGATACA|GCAGCAGTTA|GCCTCCTCGG|TGGTCCTGCA|780|
|ACAAACAGGG|ACTACTTACG|GCAGCGGCAA|GTGGCATTAG|GCAATATGGA|GACAAGGAG|840|
|TCAAAGGCTA|TACGCCAGCA|TGCAGAAGCA|GCTGGCTGTA|GCATGATTGA|AGATATTGAG|900|
|TCACCATCAT|CAATATGGGT|TTTTGCTGGA|GCACCAGACC|GTTGTCCACC|AACATGTTTG|960|
|TTTATAGCAG|GTATTGCTGA|GCTTGGGGCA|TTTTTTTCCA|TCCTGCAGGA|CATGCGAAAT|1020|
|ACAATCATGG|CATCTAAGAC|GTTGGAACAT|CTGAGGAGAA|GCTACGGAAG|AAATCATCAT|1080|

| | | | | | |
|---|---|---|---|---|---|
| TTTATCAGTC | CTACCTCAGA | AGGACACAAT | CAATGGGGAT | ACAACTAGGC | CAGAGAATTA 1140 |
| TTGTGCTCTT | CATGGTTGCC | TGGGGAAAGG | AGGCTGTGGA | CAACTTCCAC | TTAGGGGATG 1200 |
| ATATGGATCC | TGAGCTAAGG | ACACTGGCAC | AGAGCTTGAT | TGATGTCAAA | GTGAAGGAAA 1260 |
| TCTCCAACCA | AGAGCCTTTG | AAACTC | | | 1286 |